United States Patent
Goldstein et al.

(10) Patent No.: US 8,455,260 B2
(45) Date of Patent: Jun. 4, 2013

(54) TAGGED-FRAGMENT MAP ASSEMBLY

(75) Inventors: Peter Goldstein, Providence, RI (US); Franco Preparata, Providence, RI (US); Eli Upfal, Providence, RI (US)

(73) Assignee: Massachusetts Institute of Technology, Cambridge, MA (US)

( * ) Notice: Subject to any disclaimer, the term of this patent is extended or adjusted under 35 U.S.C. 154(b) by 219 days.

(21) Appl. No.: 12/732,259

(22) Filed: Mar. 26, 2010

(65) Prior Publication Data

US 2010/0261285 A1    Oct. 14, 2010

Related U.S. Application Data

(60) Provisional application No. 61/164,169, filed on Mar. 27, 2009.

(51) Int. Cl.
*G01N 33/50*     (2006.01)
(52) U.S. Cl.
USPC ................. 436/94; 436/91; 702/19; 702/20; 977/924
(58) Field of Classification Search
USPC ................. 435/6, 6.1, 6.11; 436/94, 91, 149, 436/150; 702/20, 19; 977/924
See application file for complete search history.

(56) References Cited

U.S. PATENT DOCUMENTS

| | | |
|---|---|---|
| 3,699,437 A | 10/1972 | Ur |
| H201 H | 1/1987 | Yager |
| 4,810,650 A | 3/1989 | Kell et al. |
| 4,874,499 A | 10/1989 | Smith et al. |
| 5,194,133 A | 3/1993 | Clark et al. |
| 5,202,231 A | 4/1993 | Drmanac et al. |
| 5,314,829 A | 5/1994 | Coles |
| 5,405,519 A | 4/1995 | Schwartz |
| 5,427,663 A | 6/1995 | Austin et al. |
| 5,539,082 A | 7/1996 | Nielsen et al. |
| 5,560,811 A | 10/1996 | Briggs et al. |
| 5,599,664 A | 2/1997 | Schwartz |
| 5,650,305 A | 7/1997 | Hui et al. |
| 5,681,947 A | 10/1997 | Bergstrom et al. |
| 5,683,881 A | 11/1997 | Skiena |
| 5,720,928 A | 2/1998 | Schwartz |
| 5,744,366 A | 4/1998 | Kricka et al. |
| 5,773,571 A | 6/1998 | Nielsen et al. |
| 5,795,782 A | 8/1998 | Church et al. |
| 5,824,477 A | 10/1998 | Stanley |
| 5,837,115 A | 11/1998 | Austin et al. |
| 5,908,745 A | 6/1999 | Mirzabekov et al. |
| 5,972,619 A | 10/1999 | Drmanac et al. |
| 6,015,714 A | 1/2000 | Baldarelli et al. |
| 6,020,599 A | 2/2000 | Yeo |
| 6,025,891 A | 2/2000 | Kim |
| 6,084,648 A | 7/2000 | Yeo |
| 6,100,949 A | 8/2000 | Kim |
| 6,108,666 A | 8/2000 | Floratos et al. |
| 6,128,051 A | 10/2000 | Kim et al. |
| 6,147,198 A | 11/2000 | Schwartz |
| 6,150,089 A | 11/2000 | Schwartz |
| 6,174,671 B1 | 1/2001 | Anantharaman et al. |
| 6,182,733 B1 | 2/2001 | McReynolds |
| 6,210,891 B1 | 4/2001 | Nyren et al. |
| 6,210,896 B1 | 4/2001 | Chan |
| 6,258,568 B1 | 7/2001 | Nyren |
| 6,263,286 B1 | 7/2001 | Gilmanshin et al. |
| 6,267,872 B1 | 7/2001 | Akeson et al. |
| 6,274,320 B1 | 8/2001 | Rothberg et al. |
| 6,294,136 B1 | 9/2001 | Schwartz |
| 6,303,288 B1 | 10/2001 | Furcht et al. |
| 6,304,318 B1 | 10/2001 | Matsumoto |
| 6,340,567 B1 | 1/2002 | Schwartz et al. |
| 6,355,420 B1 | 3/2002 | Chan |
| 6,362,002 B1 | 3/2002 | Denison et al. |
| 6,392,719 B2 | 5/2002 | Kim |
| 6,400,425 B1 | 6/2002 | Kim et al. |
| 6,403,311 B1 | 6/2002 | Chan |
| 6,413,792 B1 | 7/2002 | Sauer et al. |
| 6,428,959 B1 | 8/2002 | Deamer |
| 6,448,012 B1 | 9/2002 | Schwartz |
| 6,464,842 B1 | 10/2002 | Golovchenko et al. |
| 6,503,409 B1 | 1/2003 | Fleming |
| 6,509,158 B1 | 1/2003 | Schwartz |
| 6,537,755 B1 * | 3/2003 | Drmanac ..................... 435/6.11 |
| 6,537,765 B2 | 3/2003 | Stricker-Kongra et al. |
| 6,610,256 B2 | 8/2003 | Schwartz |
| 6,616,895 B2 | 9/2003 | Dugas et al. |
| 6,617,113 B2 | 9/2003 | Deamer |
| 6,627,067 B1 | 9/2003 | Branton et al. |
| 6,672,067 B2 | 1/2004 | Farmer et al. |

(Continued)

FOREIGN PATENT DOCUMENTS

DE    19936302    2/2001
EP    1486775    12/2004

(Continued)

OTHER PUBLICATIONS

International Search Report and Written Opinion dated Sep. 30, 2010, PCT/US2010/028848, 14 pgs.

(Continued)

*Primary Examiner* — Yelena G Gakh
*Assistant Examiner* — Christopher A Hixson
(74) *Attorney, Agent, or Firm* — Goodwin Procter LLP

(57) ABSTRACT

A method for determining a sequence of a biomolecule, the method including binding a plurality of uniform probes to a biomolecule fragment, creating a collection of binding signatures for the fragment with each binding signature representing a series of distances between binding sites within the fragment, and grouping the binding signatures into a plurality of signature clusters based at least in part on distances between the binding sites in each binding signature. For each binding signature in a first cluster, a potential successor binding signature is selected from signature clusters other than the first signature cluster, and one of the potential successor binding signatures is identified as a successor binding signature. The last two steps are repeated until the successor signature represents a terminal signature, resulting in a sequence of signatures representing at least a portion of the biomolecule.

14 Claims, 9 Drawing Sheets

U.S. PATENT DOCUMENTS

| | | |
|---|---|---|
| 6,673,615 B2 | 1/2004 | Denison et al. |
| 6,685,841 B2 | 2/2004 | Lopez et al. |
| 6,687,563 B1 | 2/2004 | Wang et al. |
| 6,689,563 B2 | 2/2004 | Preparata et al. |
| 6,696,022 B1 | 2/2004 | Chan et al. |
| 6,713,263 B2 | 3/2004 | Schwartz |
| 6,746,594 B2 | 6/2004 | Akeson et al. |
| 6,762,059 B2 | 7/2004 | Chan et al. |
| 6,772,070 B2 | 8/2004 | Gilmanshin et al. |
| 6,790,671 B1 | 9/2004 | Austin et al. |
| 6,818,395 B1 | 11/2004 | Quake et al. |
| 6,911,345 B2 | 6/2005 | Quake et al. |
| 6,919,002 B2 | 7/2005 | Chopra |
| 6,927,065 B2 | 8/2005 | Chan et al. |
| 6,936,433 B2 | 8/2005 | Akeson et al. |
| 7,001,792 B2 | 2/2006 | Sauer et al. |
| 7,005,264 B2 | 2/2006 | Su et al. |
| 7,034,143 B1 | 4/2006 | Preparata et al. |
| 7,071,324 B2 | 7/2006 | Preparata et al. |
| 7,118,657 B2 | 10/2006 | Golovchenko et al. |
| 7,170,050 B2 | 1/2007 | Turner et al. |
| 7,189,503 B2 | 3/2007 | Akeson et al. |
| 7,211,414 B2 | 5/2007 | Hardin et |
| 7,217,562 B2 | 5/2007 | Cao et al. |
| 7,238,485 B2 | 7/2007 | Akeson et al. |
| 7,248,771 B2 | 7/2007 | Schmidt et al. |
| 7,250,115 B2 | 7/2007 | Barth |
| 7,262,859 B2 | 8/2007 | Larson et al. |
| 7,279,337 B2 | 10/2007 | Zhu |
| 7,282,130 B2 | 10/2007 | Flory |
| 7,282,330 B2 | 10/2007 | Zhao et al. |
| 7,297,518 B2 | 11/2007 | Quake et al. |
| 7,302,146 B2 | 11/2007 | Turner et al. |
| 7,315,019 B2 | 1/2008 | Turner et al. |
| 7,329,492 B2 | 2/2008 | Hardin et al. |
| 7,351,538 B2 | 4/2008 | Fuchs et al. |
| 7,355,216 B2 | 4/2008 | Yang et al. |
| 7,371,520 B2 | 5/2008 | Zhao et al. |
| 7,402,422 B2 | 7/2008 | Fuchs et al. |
| 7,462,449 B2 | 12/2008 | Quake |
| 7,476,503 B2 | 1/2009 | Turner et al. |
| 7,476,504 B2 | 1/2009 | Turner |
| 7,501,245 B2 | 3/2009 | Quake et al. |
| 7,595,160 B2 | 9/2009 | White et al. |
| 7,678,562 B2 | 3/2010 | Ling |
| 2001/0004728 A1 | 6/2001 | Preparata et al. |
| 2002/0028458 A1 | 3/2002 | Lexow |
| 2002/0058279 A1 | 5/2002 | Fritsch et al. |
| 2002/0127855 A1 | 9/2002 | Sauer et al. |
| 2002/0137089 A1 | 9/2002 | Deamer |
| 2003/0003609 A1 | 1/2003 | Sauer et al. |
| 2003/0064095 A1 | 4/2003 | Martin et al. |
| 2003/0064382 A1* | 4/2003 | Preparata et al. ............ 435/6 |
| 2003/0080042 A1 | 5/2003 | Barth et al. |
| 2003/0104428 A1 | 6/2003 | Branton et al. |
| 2003/0143614 A1 | 7/2003 | Drmanac |
| 2003/0186256 A1 | 10/2003 | Fischer |
| 2003/0207326 A1 | 11/2003 | Su et al. |
| 2003/0211502 A1 | 11/2003 | Sauer et al. |
| 2003/0232346 A1 | 12/2003 | Su |
| 2004/0137734 A1 | 7/2004 | Chou et al. |
| 2004/0146430 A1 | 7/2004 | Dugas |
| 2004/0197843 A1 | 10/2004 | Chou et al. |
| 2005/0019784 A1 | 1/2005 | Su et al. |
| 2005/0127035 A1 | 6/2005 | Ling |
| 2006/0019247 A1 | 1/2006 | Su et al. |
| 2006/0063171 A1 | 3/2006 | Akeson et al. |
| 2006/0154399 A1 | 7/2006 | Sauer et al. |
| 2006/0269483 A1 | 11/2006 | Austin et al. |
| 2006/0287833 A1 | 12/2006 | Yakhini |
| 2007/0008051 A1 | 1/2007 | Tsuda et al. |
| 2007/0020772 A1 | 1/2007 | Cao et al. |
| 2007/0039920 A1 | 2/2007 | Kutchoukov et al. |
| 2007/0042366 A1 | 2/2007 | Ling |
| 2007/0084163 A1 | 4/2007 | Lai |
| 2007/0084702 A1 | 4/2007 | Lin et al. |
| 2007/0138132 A1 | 6/2007 | Barth |
| 2007/0178240 A1 | 8/2007 | Yamazaki et al. |
| 2007/0190542 A1 | 8/2007 | Ling et al. |
| 2007/0218471 A1 | 9/2007 | Kim et al. |
| 2007/0231795 A1 | 10/2007 | Su |
| 2007/0238112 A1 | 10/2007 | Sohn et al. |
| 2008/0041733 A1 | 2/2008 | Hibbs et al. |
| 2008/0085840 A1 | 4/2008 | Buzby |
| 2008/0096287 A1 | 4/2008 | Barth |
| 2008/0102504 A1 | 5/2008 | Akeson et al. |
| 2008/0119366 A1 | 5/2008 | Sauer et al. |
| 2008/0171316 A1 | 7/2008 | Golovchenko et al. |
| 2008/0187915 A1 | 8/2008 | Polonsky et al. |
| 2008/0234136 A1 | 9/2008 | Drmanac et al. |
| 2008/0242556 A1 | 10/2008 | Cao et al. |
| 2009/0005252 A1 | 1/2009 | Drmanac et al. |
| 2009/0011943 A1 | 1/2009 | Drmanac et al. |
| 2009/0035777 A1 | 2/2009 | Kokoris et al. |
| 2009/0099786 A1 | 4/2009 | Oliver et al. |
| 2009/0111115 A1 | 4/2009 | Drmanac et al. |
| 2009/0176652 A1 | 7/2009 | Dahl et al. |
| 2010/0078325 A1 | 4/2010 | Oliver |
| 2010/0096268 A1 | 4/2010 | Ling et al. |
| 2010/0143960 A1 | 6/2010 | Bazin |
| 2010/0297644 A1 | 11/2010 | Kokoris et al. |
| 2010/0310421 A1 | 12/2010 | Oliver et al. |

FOREIGN PATENT DOCUMENTS

| | | |
|---|---|---|
| EP | 1685407 | 8/2006 |
| WO | WO-9004652 | 5/1990 |
| WO | WO-9617957 | 6/1996 |
| WO | WO-9835012 | 8/1998 |
| WO | WO-0009757 | 2/2000 |
| WO | WO-0011220 A1 | 3/2000 |
| WO | WO-0022171 | 4/2000 |
| WO | WO-0118246 | 3/2001 |
| WO | WO-0137958 | 5/2001 |
| WO | WO-0142782 | 6/2001 |
| WO | WO-0207199 | 1/2002 |
| WO | WO-0250534 | 6/2002 |
| WO | WO-03000920 | 1/2003 |
| WO | WO-03010289 | 2/2003 |
| WO | WO-03079416 | 9/2003 |
| WO | WO-03106693 | 12/2003 |
| WO | WO-2004035211 | 4/2004 |
| WO | WO-2004085609 | 10/2004 |
| WO | WO-2005017025 | 2/2005 |
| WO | WO-2006020775 | 2/2006 |
| WO | WO-2006028508 | 3/2006 |
| WO | WO-2006052882 | 5/2006 |
| WO | WO-2007-041621 A2 | 4/2007 |
| WO | WO-2007106509 | 9/2007 |
| WO | WO-2007111924 | 10/2007 |
| WO | WO-2007127327 | 11/2007 |
| WO | WO-2008021488 | 2/2008 |
| WO | WO-2008039579 | 4/2008 |
| WO | WO-2008042018 | 4/2008 |
| WO | WO-2008046923 | 4/2008 |
| WO | WO-2008049021 | 4/2008 |
| WO | WO-2008069973 | 6/2008 |
| WO | WO-2008079169 | 7/2008 |
| WO | WO-2010111605 | 9/2010 |
| WO | WO-2010138136 | 12/2010 |
| WO | WO-2012-047589 A2 | 4/2012 |

OTHER PUBLICATIONS

Akeson, et al., "Microsecond time-scale discrimination among polycytidylic acid, polyadenylic acid, and polyuridylic acid as homopolymers or as segments within single RNA molecules," Biophys. J. 77, 3227-3233 (1999).

Alberts, B., et al., (1970) "T4 Bacteriophage Gene 32: A Structural Protein in the Replication and Recombination of DNA," Nature 227:1313-1318.

Amit, B., et al., (1974) "Photosensitive Protecting Groups of Amino Sugars and Their Use in Glycoside Synthesis. 2-Nitrobenzyloxycarbonylamino and 6-Nitroveratryloxycarbonylamino Derivatives," J. Org. Chem. 39:192-196.

Arratia, R., et al., (1989) "Poisson Process Approximation for Repeats in One Sequence and Its Application to Sequencing by Hybridization," Dept. of Mathematics, University of Southern California.

Ashkin, "Optical trapping and manipulation of neutral particles using lasers," Proc. Natl. Acad. Sci. USA, vol. 94, DD. 4853-4860, May 1997.

Austin, M., et al., (2004) "Fabrication of 5 nm Linewidth and 14 nm Pitch Features by Nanoimprint Lithography," App. Phys. Lett. 84:5299-5301.

Bains, W., et al., (1988) "A Novel Method for Nucleic Acid Sequence Determination," J. Theor. Biol. 135:303-307.

Baliga, R., et al., (2001) "Kinetic Consequences of Covalent Linkage of DNA Binding Polyamides," Biochemistry 40:3-8.

Bennett et al. Pharmacogenomics (2005) 6:373-382.

Bianco, P., et al., "Interaction of the RecA Protein of *Escherichia coli* with Single-Stranded Oligodeoxyribonucleotides," Nucleic Acids Research vol. 24. No. 24 (1996) 4933-4939.

Buchmueller, K.L., et al., (2005) "Extending the Language of DNA Molecular Recognition by Polyamides: Unexpected Influence of Imidazole and Pyrrole Arrangement on Binding Affinity and Specificity," J. Am. Chem. Soc. 127:742-750.

Buchmueller, K.L., et. al., (2006) "Physical and Structural Basis for the Strong Interactions of the -ImPy- Central Pairing Motif in the Polyamide f-ImPylm," Biochemistry 45:13551-13565.

Cao, H., et al., (2002) "Fabrication of 10 nm Enclosed Nanofluidic Channels," Applied Physics Letters 81(1): 174-176.

Cao, H., et al., (2002) "Gradient Nanostructures for Interfacing Microfluidics and Nanofluidics," Applied Physics Letters 81:3058-3060.

Chen, C., et al., (1994) "Analogous Organic Synthesis of Small-Compound Libraries: Validation of Combinatorial Chemistry in Small-Molecule Synthesis," J. Am. Chem. Soc. 116:2661-2662.

Chen, P., et al., (2004) "Probing Single DNA Molecule Transport Using Fabricated Nanopores," Nano Letters 4:2293-2298.

Chetverin, A., et al., (1994) "Oligonucleotide Arrays: New Concepts and Possibilities," Bio/Technology 12:1093-1099.

Cox, M. (2007) "Motoring Along with the Bacterial RecA Protein," Nature Reviews—Molecular Cell Biology 9:127-138.

Dervan, P.B. (2001) "Molecular Recognition of DNA by Small Molecules," Bioorg. Med. Chem. 9:2215-2235.

Dervan, P.B., et al., (2003) "Recognition of the DNA minor groove by pyrrole-imidazole polyamides," Curr. Op. Struc. Biol. 13:284-299.

Doss, R.M., et al., (2006) "Programmable Oligomers for Minor Groove DNA Recognition," J. Am. Chem. Soc. 128:9074-9079.

Drmanac, R., et al. (1989) "Sequencing of Megabase Plus DNA by Hybridization: Theory of the Method," Genomics 4:114-128.

Ellervik, U., et al., (2000) "Hydroxybenzamide/Pyrrole Pair Distinguishes T-A from A-T Base Pairs in the Minor Groove of DNA," J. Am. Chem. Soc. 122:9354-9360.

Farkas, Z., et al., (2003) "DNA Uptake Into Nuclei: Numerical and Analytical Results," J. Phys.: Condens. Matter 15:S1767-S1777.

Fechter, E.J., et al., (2005) "Sequence-specific Fluorescence Detection of DNA by Polyamide-Thiazole Orange Conjugates," J. Am. Chem. Soc. 127:16685-16691.

Floreancig, P.E., et al., (2000) "Recognition of the Minor Groove of DNA by Hairpin Polyamides Containing α-Substituted-, β-Amino Acids," J. Am. Chem. Soc. 122:6342-6350.

Fodor, S., et al., (2005) "Light-Directed, Spatially Addressable Parall Chemical Synthesis" Research Article 6 pgs.

Fologea, D., et al., (2005) "Slowing DNA Translocation in a Solid-State Nanopore," Nano Lett. 5(9):1734-7.

Frieze, A., et al., (1999) "Optimal Reconstruction of a Sequence From its Probes," 12 pgs.

Gerland, U., et al., (2004) "Translocation of Structured Polynucleotides Through Nanopores," Phys. Biol. 1:19-26.

Gershow, M., et al., (2007) "Recapturing and Trapping Single Molecules with a Solid-State Nanopore," Nature Nanotech. 2:775-779.

Gracheva, M., et al., (2002) "Simulation of the Electric Response of DNA Translocation through a Semiconductor Nanopore-Capacitor," Nanotechnology 17:622-633.

Guo, L. (2004) "Recent Progress in Nanoimprint Technology and its Application," J. Phys. D: Appl. Phys 37:R123-R141 (Appendices B-D).

Gygi, M.P., et al., (2002) "Use of fluorescent sequence-specific polyamides to discriminate human chromosomes by microscopy and flow cytometry," Nucleic Acids Research 30:2790-2799.

Halby, L., et al., (2005) "Functionalized head-to-head hairpin polyamides: Synthesis, double-stranded DNA-binding activity and affinity," Bioorg. Med. Chem. Lett. 15:3720-3724.

Heller, C., (2001) "Principles of DNA Separation with Capillary Electrophoresis," Electrophoresis 22:629-643.

Heng, J., et al., (2004) "Sizing DNA Using a Nanometer-Diameter Pore," Biophysical Journal 87:2905-2911.

Hudson, B., (1999) "An Experimental Study of SBH with Gapped Probes," 50 pgs.

International Search Report for PCT/US04/04138, mailed May 4, 2006, 5 pages.

International Search Report and Written Opinion dated May 2, 2009, PCTUS2008/078432.

International Search Report and Written Opinion for PCT/US09/558876 dated Feb. 10, 2010.

International Search Report and Written Opinion dated Mar. 24, 2010 for PCT/US09/055878, 13 pages.

Jonsson, U., et al., (1991) "Real-Time Biospecific Interaction Analysis Using Surface Plasmon Resonance and a Sensor Chip Technology," BioTechniques, 11:620-627.

Ju et al., Proc. Nat. Acad. Sci. USA (2006) 103:19635-19640.

Kalaugher, L., (2002) "Diffraction Gradient Lithography Aids Nanofluidics," Nanotechweb.org.

Kanehisa, L. (1984) "Use of Statistical Criteria for Screening Potential Homologies in Nucleic Acid Sequences," Nucleic Acids Research 12:203-213.

Kasianowicz et al., "Characterization of Individual Polynucleotide Molecules Using a Membrane Channel," Proc. Nat. Acad. Sci. USA 93:13770-13773 (1996).

Khrapko, K.R. et al., (1989) "An Oligonucleotide Hybridizatioin Approach to DNA Sequencing," FEBS Lett. 256:118-22.

Kim, C., et al., (1992) "Binding Properties of Replication Protein A from Human and Yeast Cells," Mol. and Cell. Bio. 12(7):3050-3059.

Kuo, et al., "Hybrid three-dimensional nanofluidic/microfluidic devices using molecular gates," Sensors and Actuators A, vol. 102 (Oct. 2002):223-233.

Langa, "Self-organized growth of single crystals of nanopores," Applied Physics Letters, AIP, American Institute of Physics, 2003, vol. 82, No. 2, pp. 278-280.

Li et al., "Lon-beam sculpting at nanometre length scales", Nature 412,166-169 (2001).

Liang, X., et al., (2007) "Single Sub-20 nm wide Centimeter-Long NanoFluidic Channel Fabricated by Novel Nanoimprint Mold Fabrication and Divest Imprinting," Nano Letters 7:3774-3780.

Liang, X., et al., (2008) "Nanogap Detector Inside Nanofluidic Channel for Fast Real Time Label-Free DNA Analysis," Nano Letters 8:1472-76.

Loakes, D., et al., (1994) "5-Nitroindole as an Universal Base Analogue," Nucleic Acids Research 22:4039-4043.

Loakes, D., et al., (1995) "3-Nitropyrrole and 5-Nitroindole as Universal Bases in Primers for DNA Sequencing and PCR," 23:2361-2366.

Lohman, T., et al., (1994) "*Escherichia coli* Single-Stranded DNA-Binding Protein: Multiple DNA-Binding Modes and Cooperatives," Annu. Rev. Biochem. 63:527-70.

Losi, et al., "Time-Resolved Absorption and Photothermal Measurements with Recombinant Sensory Rhodopsin II from *Natronobacterium pharaonis*," Biophys. J. 77, 3277-3286, Dec. 1999.

Lysov,Y.P., et al., (1988) "Determination of the Nucleotide Sequence of DNA Using Hybridization with Oligonucleotides. A New Method," Dokl. Acad. Nauk SSSR 303:1508-1511 [Article in Russian].

Margulies et al., (2005) Nature 437:376-380.

Marques, M.A., et al., (2004) "Expanding the Repertoire of Heterocycle Ring Pairs for Programmable Minor Groove DNA Recognition," J. Am. Chem. Soc. 126:10339-10349.

McEntee, K., et al. "Binding of the RecA Protein of *Escherichia coli* to Single- and Double-Stranded DNA." J. Biol. Chem. (1981) 256:8835.

Meller, A., et al., (2000) "Rapid Nanopore Discrimination Between Single Polynucleotide Molecules," PNAS 97:1079-1084.
Meller, et al., "Voltage-driven DNA translocations through a nanopore," Phys. Rev. Lett. 86(15),3435-3438 (2001).
Nice, E., et al., (1993) "Mapping of the Antibody- and Receptor-Binding Domains of Granulocyte Colony-Stimulating Factor Using an Optical Biosensor," Journal of Chromatography 646:159-168.
Nichols, R., et al., (1994) "A Universal Nucleoside for Use at Ambiguous Sites in DNA Primers," Letters to Nature 369:492-493.
Novopashina, D.S., et al., (2005) "Sequence-Specific Conjugates of Oligo(2'-O-methylribonucleotides) and Hairpin Oligocarboxamide Minor-Groove Binders: Design, Synthesis, and Binding Studies with Double-Stranded DNA," Chemistry & Biodiversity 2:936-952.
Optical Tweezers: Introduction to Optical Tweezers, Retrieved Apr. 21, 2010 from http://www.nbi.dk/~tweezer/introduction.htm, pp. 1-5.
Pablo, P.J., et al., (2000) "Absence of dc-Conductivity." Phys. Rev. Lett. 85:4992-4995.
Partial International Search Report dated Feb. 15, 2010 for PCT/US09/055878, 3 pages.
Perry, J., et al., (2005) "Review of Fabrication of Nanochannels for Single Phase Liquid Flow," 3rd Intl. Conference on Microchannels and Minichannels, Paper No. ICMM2005-75104.
Pevzner, P. et al., (1991) "Improved Chips for Sequencing by Hybridization," Journal of Biomolecular Structure & Dynamics 9:399-410.
Pevzner, P., (1989) "1-Tuple DNA Sequencing: Computer Analysis," Journal of Biomolecular Structure & Dynamics 7:63-73.
Powell, M., et al., (1993) "Characetrization of the Pf3 Single-Strand DNA Binding Protein by Circular Dichroism Spectroscopy," Biochemistry 32:12538-12547.
Preparata, F., et al., (1999) "On the Power of Universal Bases in Sequencing by Hybridization," 7 pgs.
Preparata, F.P., et. al., (2000) "Sequencing-by-Hybridization at the Information-Theory Bound: An Optimal Algorithm," J. Comp. Biol. 7: 621-630.
Quake et al. Proc. Nat. Acad. Sci. USA (2003) 100:3960-3964.
Riehn, R. et al., (2005) Proc. Nat. Acad. Sci., 102:1012.
Robertson, J., et al., (2007) "Single-Molecule Mass Spectrometry in Solution Using a Solitary Nanopore," PNAS 104:8207-8211.
Rucker, V.C., et al., (2003) "Sequence Specific Fluorescence Detection of Double Strand DNA," J. Am. Chem. Soc. 125:1195-1202.
Sanger, F. et al., (1977) "DNA Sequencing with Chain-Terminating Inhibitors," Proc. Natl. Acad. Sci. USA 12:5463-5467.
Shinohara. Y., et al., (1995) "Use of a Biosensor Based on Surface Plasmon Resonance and Biotinyl Glycans for Analysis of Sugar Binding Specificities of Lectins," J. Biochem, 117:1076-1082.
Singer, E. (2008) "The $100 Genome," Technology Review 4 pgs.
Smeets, R., et al., (2008) "Translocation of RecA-Coated Double-Stranded DNA through Solid-State Nanopores," Nano Letters pp. A-G.
Southern, E.M. (1996) "DNA Chips: Analysing Sequence by Hybridization to Oligonucleotide on a Large Scale," Trends in Genetics 12(3):110-115.
Storm, et al., "Fabrication of solid-state nanopores with single-nanometre precision," Nature Materials 2,537-540, Auaust 2003.
Storm, A., et al., (2005) "Fast DNA Translocation through a Solid-State Nanopore," Nano Letters 5(7):1193-1197.
Strezoska, Z., et al., (1991) "DNA Sequencing by Hybridization: 100 Bases Read by a Non-Gel-Based Method," Proc. Natl. Acad. Sci. USA 88:10089-10093.
Tegenfeldt, J., et al., (2004) "The Dynamics of Genomic-Length DNA Molecules in 100 nm Channels," Proc. Nat. Acad. Sci. USA 101:10979-10983.
Tersoff, "Less is more," Nature 412, 135-136, Jul. 2001.
Terwilliger, T., et al., (1996) "Gene V Protein Dimerization and Cooperativity of Binding to Poly (dA)," Biochemistry 35:16652-16664.
Tucker, P., et al., (1994) "Crystal Structure of the Adenovirus DNA Binding Protein a Hook-On Model for Cooperative DNA Binding," The EMBO Journal 13(13):2994-3002.

Urbach, A.R., (2001) "Toward rules for 1:1 polyamide:DNA recognition," PNAS 98:4343-4348.
Warren, C.L., et al., (2006) "Defining the Sequence-Recognition Profile of DNA-Binding Molecules," PNAS 103:867-872.
Warren, S., (1996) "The Expanding World of Trinucleotide Repeats," Science 271:1374-1375.
Web article (2003) "DNA Combed Into Nanochannels," http://www.nature.com.
Written Opinion dated Jul. 1, 2008, PCT/US06/38748.
Zhang, W., et al., (2006) "Discrimination of Hairpin Polyamides with an α-Substituted-γ-aminobutyric Acid as a 5'-TG-3' Reader in DNA Minor Groove," J. Am. Chem. Soc. 128:8766-8776.
Zwolak, M., et al., (2008) "Physical Approaches to DNA Sequencing and Detection." Rev. Mod. Phy. 80:141-165 (J).
Giehart B., et al., (2008) "Nanopore with transverse nanoelectrodes for electrical characterization and sequencing of DNA" Sensors and Actuators B., Elsevier Sequoia S.A, ScienceDirect,132:2.
International Search Report and Written Opinion dated Jun. 29, 2010, PCT/US09/055876, 13 pages.
Invitation to Pay Additional Fees and, Where Applicable, Protest Fee & Partial International Search dated Aug. 19, 2010, PCT/US2010/028848, 7 pages.
Ben-Dor et al, "On the Complexity of Positional Sequencing by Hybridization", Journal of Computational Biology, vol. 8, No. 4, 2001, pp. 361-371.
Bloom, et al, Applications of Numbered Undirected Graphs, Proceedings of the IEEE, vol. 65, No. 4, Apr. 1977, pp. 562-570.
Branton, Daniel et al, "The potential and challenges of nanopore sequencing," Nature Biotechnology, vol. 26, No. 10, Oct. 2008, pp. 1146-1153.
International Preliminary Report on Patentability, issuance of report Mar. 8, 2011, Application No. PCT/US2009/055876.
International Preliminary Report on Patentability, Application No. PCT/US2009/055878, mailed Dec. 8, 2011, 10 pages.
International Preliminary Report on Patentability, PCT/US2008/078432, issuance date Apr. 7, 2010.
International Search Report and Written Opinion, PCT/US2011/059933, dated Apr. 2, 2012.
Austin, Robert, "The art of sucking spaghetti", Nature Publishing Group, Nature Materials, vol. 2, pp. 567-568, Sep. 2003.
Bourdoncle, A., et al., "Quaruplex-Based Molecular Beacons as Tunable DNA Probes", J. Am. Chem. Soc., vol. 128, No. 34, pp. 11094-11105, 2006.
Drmanac, R., et al. (2002) "Sequencing by Hybridization (SBH): Advantages, Achievements, and Opportunities," Advances in Biochemical Engineering/Biotechnology, vol. 77: 75-101.
Ghosh, et al, Detection of Double-Stranded DNA: molecular methods and applications for DNA diagnostics Molecular Biosystems (2006) vol. 2, pp. 551-560.
International Preliminary Report on Patentability, Application No. PCT/US2010/028848, issuance date Sep. 27, 2011, 8 pages.
International Search Report and Written Opinion dated Feb. 5, 2009, PCT/US08/078432.
Invitation to Pay Additional Fees and, Where Applicable, Protest Fee & Partial International Search dated Jul. 10, 2012, PCT/US2012/024708, 10 pages.
Lennon, Erwan et al., "Evaporative Pumping of Liquid in Nanochannel for Electrical Measurement of a Single Biomolecule in Nanofluidic Format", Proceedings of the 7th IEEE Internation Conference on Nantechnology, Hong Kong, Aug. 2-5, 2007.
Rapley, Ralph, "Enhancing PCR Amplification and Sequencing Using DNA-Binding Proteins", Molecular Biotechnology, vol. 2, pp. 295-298, 1994.
Riccelli, P. V. et al., "Hybridization of single-stranded DNA targets to immobilized complementary DNA probes: comparison of hairpin versus linear capture probes", Oxford University Press, Nucleic Acids Research, vol. 29, No. 4, pp. 996-1004, 2001.
International Search Report and Written Opinion dated Oct. 25, 2012, PCT/US12/024708.

* cited by examiner

SEQUENCE LISTING

```
<160> NUMBER OF SEQ ID NOS: 3

<210> SEQ ID NO 1
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cttctagatt ctag                                                        14

<210> SEQ ID NO 2
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
cuucuagauu cuag                                                        14

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
aattctaaca ttcta                                                       15
```

TAGGED-FRAGMENT MAP ASSEMBLY

CROSS REFERENCE TO RELATED APPLICATION

This application claims the benefit of priority under 35 U.S.C. §119(e) to U.S. Provisional Application Ser. No. 61/164,169, filed Mar. 27, 2009, the entirety of which is incorporated herein by reference.

SEQUENCE LISTING

The instant application contains a Sequence Listing which has been submitted via EFS-Web and is hereby incorporated by reference in its entirety. Said ASCII copy, created on May 5, 2010, is named NAB-005 txt and is 994 bytes in size.

TECHNICAL FIELD

The present invention relates generally to biomolecule sequencing. More particularly, in certain embodiments, the invention relates to methods of biomolecule sequencing involving creating binding signature clusters for the biomolecule, and selecting potential successor binding signature from other binding signature clusters.

BACKGROUND

Identifying the composition and sequence of various biomolecules, such as human DNA, with accuracy and specificity is of great interest. Sequencing technology, however, is time consuming and expensive to develop and implement. For example, sequencing the DNA of a single individual for the Human Genome Project required over $3 billion of funding.

It is estimated that each person's DNA varies from one another by approximately 1 base in 1000. Knowledge of such genetic variations among human populations may allow the scientific community to identify genetic trends that are related to various medical predispositions, conditions, or diseases, and may lead to the realization of truly personalized medicine where treatments are customized for a given individual based on that individual's DNA. A reduction in the time and cost of DNA sequencing is needed to develop such knowledge and to tailor medical diagnostics and treatments based on the genetic makeup of individual patients.

Hybridization Assisted Nanopore Sequencing (HANS) is a nanopore-based method for sequencing genomic lengths of DNA and other biomolecules. The method relies on detecting the position of hybridization of probes on specific portions of the biomolecule to be sequenced or characterized.

In this method, two reservoirs of solution are separated by a nanometer-sized hole, or nanopore, that serves as a fluidic constriction of known dimensions. The application of a constant DC voltage between the two reservoirs results in a baseline ionic current that is measured. If an analyte is introduced into a reservoir, it may pass through the fluidic channel and change the observed current, due to a difference in conductivity between the electrolyte solution and analyte. The magnitude of the change in current depends on the volume of electrolyte displaced by the analyte while it is in the fluidic channel. The duration of the current change is related to the amount of time that the analyte takes to pass through the nanopore constriction. The current signals are used in determining the position of the probes on the biomolecule by use of computer algorithms. Aligning the probe positions allows for sequencing the biomolecule. Efficient algorithms are needed for sequencing.

SUMMARY OF THE INVENTION

In a first aspect, embodiments of the invention include a method for sequencing a biomolecule, such as a single or double-stranded DNA molecule, RNA molecule or other similar biomolecules. The method includes the steps of creating a biomolecule fragment from the biomolecule and binding probes to the biomolecule fragment. The sites at which the probe bound to the fragment are identified. Binding signatures are created, where each binding signature represents a series of distances between binding sites within the fragment. The binding signatures are grouped into clusters based, for example, on measured distances (e.g., the number of base pairs) between the binding sites in each binding signature and/or a degree of match between the binding sites attributed to the binding signatures. For each binding signature in a selected cluster, a potential successor binding signature is identified from other signature clusters. The process is repeated the successor signature represents a terminal signature, resulting in a sequence of signatures representing at least a portion of the biomolecule.

In some embodiments, the method also includes measuring the distances between the binding sites within the fragment by, in one example, measuring electrical signals emitted by the fragment as the fragment passes through a nanopore. The measurement may also include assigning an error to each measured distance between binding sites. The signatures may be collected and ordered based on one or more characteristics of the signatures, such as the total length of the signatures. The probes may include 6-mer probes, 7-mer probes, 8-mer probes and 9-mer probes.

In another aspect, embodiments of the invention include a system for sequencing a biomolecule. The system includes an identifying module that identifies a plurality of binding sites along a fragment of the biomolecule at which probes are bound thereto, and a signature-creating module that creates a collection of binding signatures for the fragment. Each binding signature represents a series of distances between binding sites within the fragment. The system also includes a grouping module that groups the binding signatures into signature clusters based, for example, on distances between the binding sites in each binding signature and a selecting module that selects, for each binding signature in a first cluster, a potential successor binding signature from other signature clusters. A sequencing module identifies one of the potential successor binding signatures as a successor binding signature, and determines the sequence of at least a portion of the biomolecule based at least in part on a series of identified successor binding signatures.

In another aspect, embodiments of the invention include an article of manufacture having a computer-readable medium with computer-readable instructions embodied thereon for performing the methods and implementing the systems described in the preceding paragraphs. In particular, the functionality of a method of the present invention may be embedded on a computer-readable medium, such as, but not limited to, a floppy disk, a hard disk, an optical disk, a magnetic tape, a PROM, an EPROM, CD-ROM, or DVD-ROM or downloaded from a server. The functionality of the techniques may be embedded on the computer-readable medium in any number of computer-readable instructions, or languages such as, for example, FORTRAN, PASCAL, C, C++, Java, C#, Tcl, BASIC and assembly language. Further, the computer-readable instructions may, for example, be written in a script, macro, or functionally embedded in commercially available software (such as, e.g., EXCEL or VISUAL BASIC).

In yet another aspect, embodiments of the invention include an apparatus for sequencing a biomolecule. The apparatus includes a memory for storing code that defines a set of instructions, and a processor for executing the set of instructions to perform the following steps. A plurality of binding sites along a fragment of the biomolecule at which a plurality of uniform probes are bound are identified. A collection of binding signatures for the fragment is created, each binding signature representing a series of distances between binding sites within the fragment. The binding signatures are grouped into a plurality of signature clusters based at least in part on distances between the binding sites in each binding signature. For each binding signature in a first cluster, a potential successor binding signature from signature clusters other than the first signature cluster is selected. One of the potential successor binding signatures as a successor binding signature is identified. The sequence of at least a portion of the biomolecule is determined based at least in part on a series of identified successor binding signatures.

DETAILED DESCRIPTION

Figure 1:
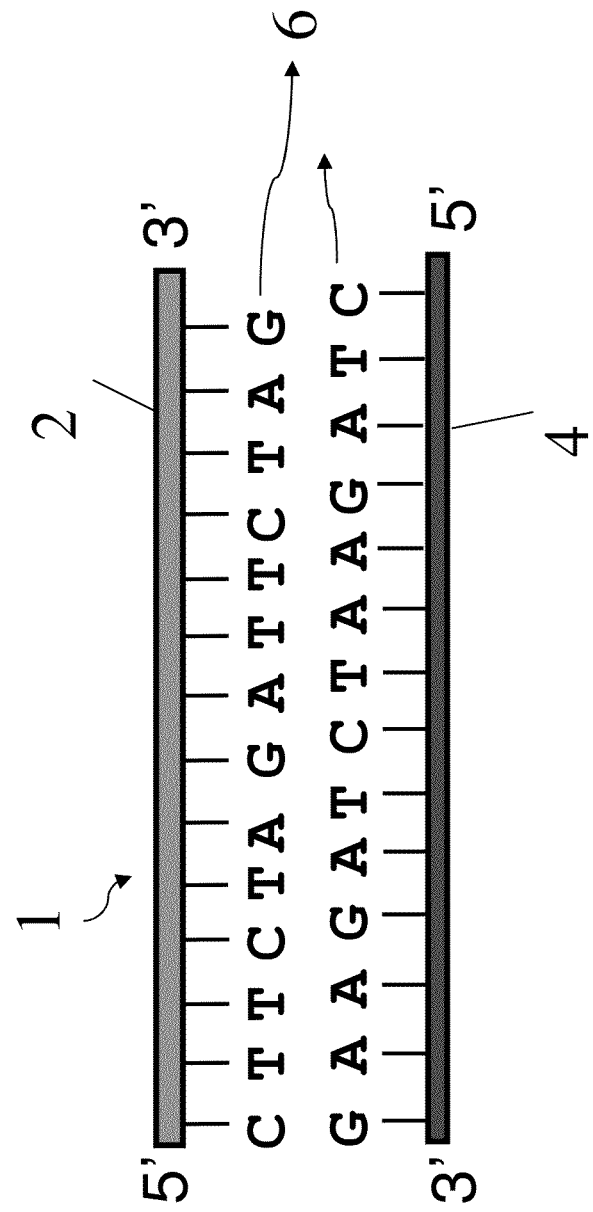
FIG. 1 is a schematic depiction of a DNA molecule (SEQ ID NO: 1)

As used in this description and the accompanying claims, the following terms shall have the meanings given, unless the context indicates otherwise:

A "target" means a biomolecule, for example, having sequence information that is to be determined using embodiments of the present invention. The target may be a biomolecule such as deoxyribonucleic acid, a ribonucleic acid, proteins, or polypeptides. The target may be single- or double-stranded.

A "probe" means any molecule or assembly of molecules capable of sequence-specific covalent or non-covalent binding to a target molecule.

A "tag" means a moiety that is attached to a probe in order to make the probe more visible to a detector. These tags may be proteins, double-stranded DNA, single-stranded DNA or other molecules. Another useful tag may be a dendrimer. Tags have either a larger volume than the probe or a different charge so that they slow translocation of the biomolecule through the nanopore.

In connection with a target bound to one or more probes, a "ternary complex" means a complex formed from three or more biomolecules. For example, a complex of two complementary strands of DNA (i.e., double-stranded DNA or dsDNA) with a third probe strand is a ternary complex. Higher order complexes also include ternary complexes; for example, a complex of double-stranded target DNA with two probe molecules bound to the same stretch of sequence, with two probe molecules bound to each other and in turn to a stretch of sequence, with two identical probe molecules bound to different subsequences, or with a probe molecule and a protein bound to a stretch of sequence are quaternary complexes that also include a ternary complex.

A "local ternary complex" means a ternary complex that is localized to a particular stretch of biopolymer. For example, multiple local ternary complexes may exist when probe molecules bind to a target molecule in multiple locations separated by stretches of bases to which the probe is not bound (i.e., uncomplexed regions).

A "polyamide" refers to the class of DNA binding polyamides originally developed by the Dervan laboratory at the California Institute of Technology. Polyamides are molecules containing heterocycle ring structures that can be combined in a modular fashion to recognize DNA sequences by binding in the minor groove of duplex DNA. Typical heterocycle ring structures in this class include, but are not limited to, N-methylimidazole, N-methylpyrrole, 3-hydroxy-N-methylpyrrole, N-methylpyrazole, 3-methylthiophene, benzimidazole, hydroxybenzimidazole, and imidazopyridine. The rings may be connected via carboxamide linkages, by the amino acid β-alanine, or directly joined by single bonds. Other ring structures and linkages can be envisaged by practitioners familiar with the art.

The polyamides may include spacers that are not sequence specific and that allow the curvature of the polyamide to stay in register with the curvature of double-stranded DNA ("gapped polyamides"). The spacer may be used as a gap when the polyamide is used as a probe for sequence determination. Gapped probes are more efficient at reconstructing sequence information than a non-gapped probe.

In connection with a target and a probe, a "probe map" means a data set containing information related to the sites along a target sequence at which a probe preferentially binds. The data set may include absolute positional information referenced to a known sequence, relative information related to distances between binding sites, or both. The data set may be stored in computer media.

A "spectrum map" means a collection of probe maps determined for a target sequence.

A "probe recognition site" refers to a target sequence, structure, or conformation that is preferentially recognized by the probe in the presence of other target sequences, structures, or conformations. The probe may interact with the recognition site through non-covalent, covalent, or mixtures of covalent and non-covalent interactions.

In connection with a probe map or a spectrum map, "dynamically weighted spectrum" means the collection of probes under consideration for the extension of a growing sequence with weights as to the likelihood that they should be chosen next. These weights may be based on a parameter related to the measured positions of the probes. The dynamically weighted spectrum may or may not include sequence information. For example, in the case of six-mers, if the growing sequence ends in ATACG, the dynamically weighted spectrum may include only the probes ATACGA, ATACGC, ATACGG, and ATACGT with weights based on their (relative) positions. Alternatively, the dynamically weighted spectrum may be thought of as a collection of probes, independent of sequence, whose probability of being next in the sequence is based on their measured distances from the current growing end of the strand. (In this case, sequence-specific information may be incorporated subsequently.)

Figure 2:
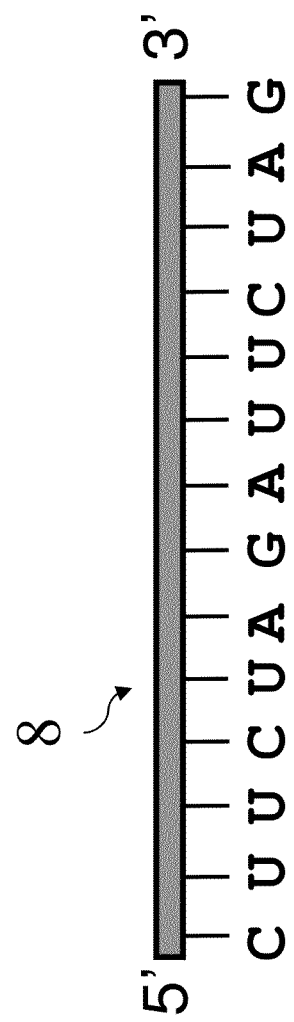
FIG. 2 is a schematic depiction of an RNA molecule (SEQ ID NO: 2)

In one embodiment, the process of sequencing a biomolecule such as DNA using one or more probes may performed as follows. Referring to FIG. 1, a DNA molecule 1 is schematically depicted and is structured in two strands 2, 4 positioned in anti-parallel relation to one another. Each of the two opposing strands 2, 4 may be sequentially formed from repeating groups of nucleotides 6 where each nucleotide 6 consists of a phosphate group, 2-deoxyribose sugar and one of four nitrogen-containing bases. The nitrogen-containing bases include cytosine (C), adenine (A), guanine (G) and thymine (T). DNA strands 2 are read in a particular direction, from the top (called the 5' or "five prime" end) to the bottom (called the 3' or "three prime" end). Similarly, RNA molecules 8, as schematically depicted in FIG. 2, are polynucleotide chains, which differ from those of DNA 1 by having ribose sugar instead of deoxyribose and uracil bases (U) instead of thymine bases (T).

Traditionally, in determining the particular arrangement of the bases 6 and thereby the sequences of the molecules, a process called hybridization may be utilized. The hybridization process is the coming together, or binding, of two genetic sequences with one another. This process is predictable because the bases 6 in the molecules do not share an equal affinity for one another. T (or U) bases favor binding with A bases while C bases favor binding with G bases. Binding is mediated via hydrogen bonds that exist between the opposing base pairs. For example, A binds to T (or U) base using two hydrogen bonds, while C binds to G using three hydrogen bonds.

Figure 3:
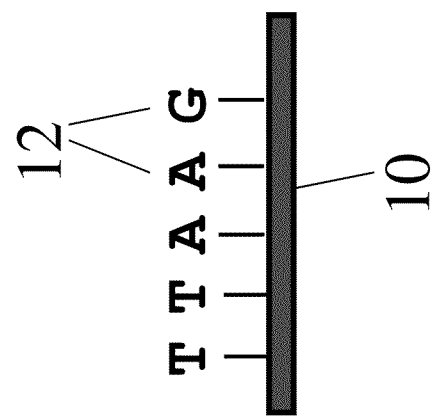
FIG. 3 is a schematic depiction of a hybridizing oligonucleotide (probe)

A hybridizing oligonucleotide, i.e., a probe 10 may be used to determine and identify the sequence of bases 6 in the molecule of interest. FIG. 3 illustrates a probe 10 that is a short DNA sequence having a known composition. Probes 10 may be of any length depending on the number of bases 12 that they include. For example, a probe 10 that includes six bases 12 is referred to as a six-mer wherein each of the six bases 12 in the probe 10 may be any one of the known four natural base types A, T(U), C or G and alternately may include non-natural bases.

In this regard, the total number of unique probes 10 in a library is dependent upon the number of bases 12 contained within each probe 10 and the number of different types of bases in the probes. If only the four natural bases are used in probe 10, the total number of probes in the library is determined by the formula $4^n$ (four raised to the n power) where n is equal to the total number of bases 12 in each probe 10. Formulas for other arrangements or types of bases are well known in the art. Accordingly, the size of the probe library can be expressed as $4^n$ n-mer probes 10. For the purpose of illustration, in the context of a six-mer probe, the total number of possible unique, identifiable probe combinations includes $4^6$ (four raised to the sixth power) or 4096 unique six-mer probes 10. The inclusion of non-natural bases allows for the creation of probes that have spaces or wildcards therein in a manner that expands the versatility of the library, while reducing the number of probes that may be needed to reach the final sequence result. Probes that include universal bases organized into patterns with natural bases may also be used, for example those described in U.S. Pat. Nos. 7,071,324, 7,034,143, and 6,689,563, incorporated in their entireties by reference herein.

Figure 4:
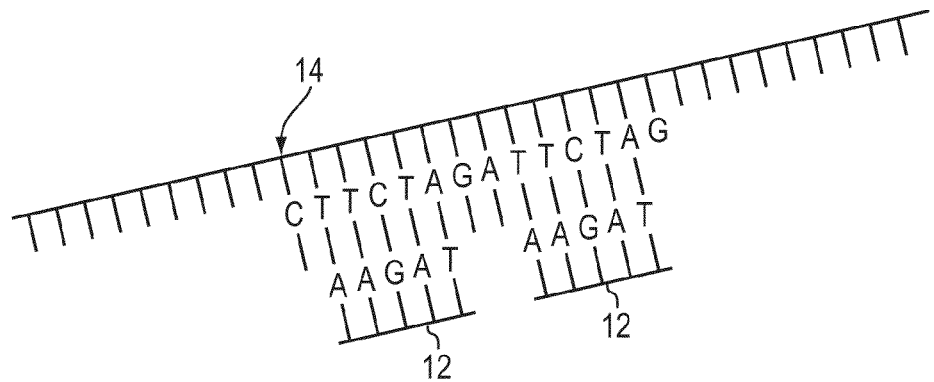
FIG. 4 is a schematic depiction of a single-stranded DNA molecule (SEQ ID NO: 1) hybridized with a probe.

The process of hybridization using probes 12, as depicted in FIG. 4, may begin by denaturing the biomolecule strand. Denaturing is accomplished usually through the application of heat or chemicals, such that the hydrogen bonds between adjacent portions of the biomolecule are broken. For example, the hydrogen bonds between the two halves of the original double-stranded DNA may be broken, leaving two single strands of DNA whose bases are now available for hydrogen bonding. After the biomolecule 14 has been denatured, a single-stranded probe 12 may be introduced to the biomolecule 14 to locate portions of the biomolecule 14 that have a base sequence that correlates to the sequence that is found in the probe 12. In order to hybridize the biomolecule 14 with the probe 12, the denatured biomolecule 14 and a plurality of the probes 12 having a known sequence are both introduced into a solution. The solution may be an ionic solution, such as a salt-containing solution. The mixture may be agitated to facilitate binding of the probes 12 to the biomolecule 14 strand along portions thereof that have a matched complementary sequence. Hybridization of the biomolecule 14 using the probe 12 may be accomplished before the biomolecule 14 is introduced into a nanopore sequencing apparatus or after the denatured biomolecule 14 has been placed into the cis chamber of the apparatus described below. In this case, after the denatured biomolecule has been added to the cis chamber, buffer solution containing probes 12 with a known sequence is also added to the cis chamber and allowed to hybridize with the biomolecule 14 before the hybridized biomolecule is translocated.

Once the biomolecule strand 14 and probes 12 have been hybridized, the strand 14 is introduced to one of the chambers of a nanopore sequencing arrangement 18. While the hybridization may be accomplished before placing the biomolecule strand 14 into the chamber, it is also possible for the hybridization to be carried out in one of these chambers as well.

Figure 5:
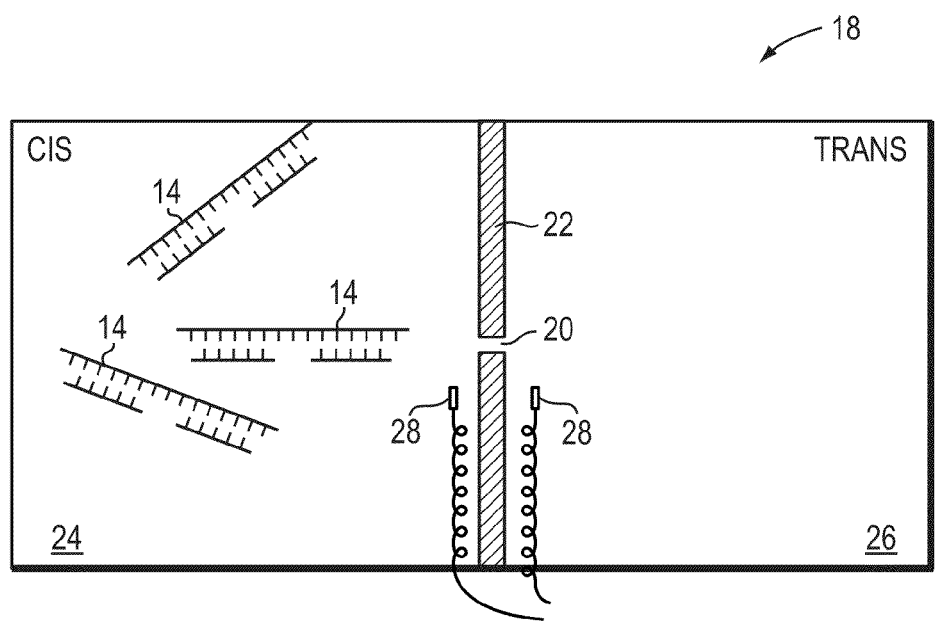
FIG. 5 is a schematic depiction of an apparatus employed in a disclosed method.

An embodiment of a nanopore sequencing arrangement 18 is graphically depicted in FIG. 5. For the purpose of illustration, relatively short biomolecule strands 14 with only two probes 12 are depicted. Long stranded biomolecule 14 may be translocated through the nanopore 20 to determine the location of the probes 12 attached thereto. The sequencing arrangement 18 includes a nanopore 20 formed in a thin wall or membrane 22. For example, the nanopore 20 may be formed in a solid-state material. Further, the nanopore 20 may have a diameter that allows the passage of double-stranded DNA and is between approximately 1 nm and 100 nm, such as between 2.3 nm and 100 nm, such as between 2.3 nm and 50 nm, e.g., 30 nm. Translocation of RecA coated DNA through a nanopore may be accomplished with pores that have diameters larger than 8 nm. The nanopore 20 is positioned between two fluid chambers, a cis chamber 24 and a trans chamber 26, each of which is filled with a fluid. The cis chamber 24 and the trans chamber 26 are in fluid communication with one another via the nanopore 20 located in the membrane 22. A voltage is applied across the nanopore 20. This potential difference between the chambers 24, 26 on opposing sides of the nanopore 20 results in a measurable ionic current flow across the nanopore 20. In one embodiment, an electrode 28 may be installed into each of the cis 24 and trans 26 chambers to apply an electrical potential and measure the flow of ion current across the nanopore 20. In an embodiment, the electrode in the cis chamber is a cathode, and the electrode in the trans chamber is an anode.

Figure 6:
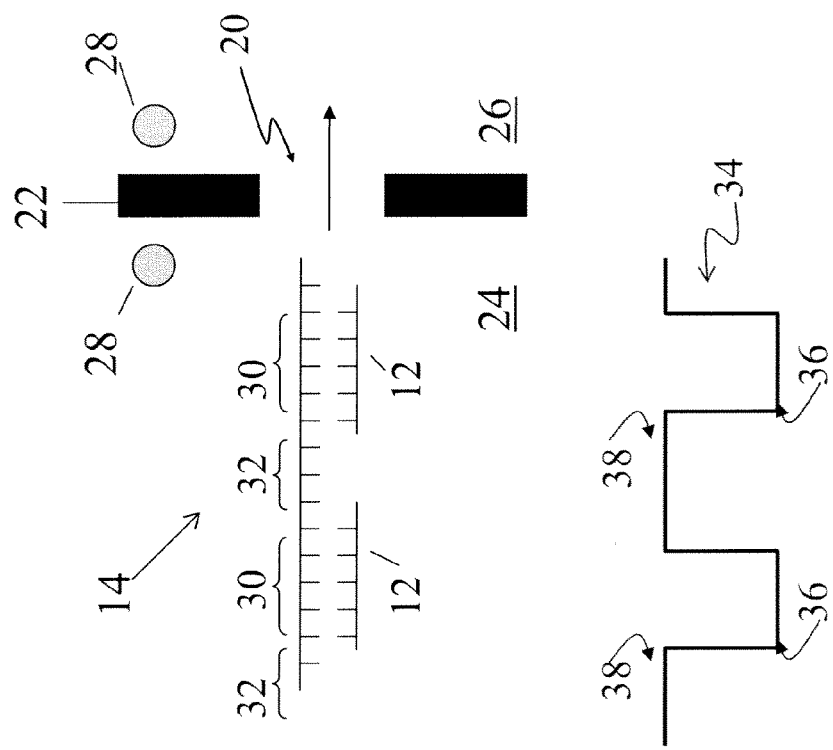
FIG. 6 is a close-up view of a hybridized biomolecule translocating through the nanopore of the apparatus in FIG. 5.

The hybridized biomolecule strand 14 with the probes 12 attached thereto is then introduced into the cis chamber in which the cathode is located. The biomolecule 14 is then driven or translocated through the nanopore 20 as a result of the applied voltage. As the molecule 14 passes through the nanopore 20, the monitored current varies by a detectable and measurable amount. The electrodes 28 detect and record this variation in current as a function of time. As shown in FIG. 6, these variations in current are the result of the relative diameter of the molecule 14 that is passing through the nanopore 20 at any given time. For example, the portions 30 of the biomolecule 14 that have probes 12 bound thereto are twice the diameter as compared to the portions 32 of the biomolecule 14 that have not been hybridized and therefore lack probes 12. This relative increase in volume of the biomolecule 14 passing through the nanopore 20 causes a temporary interruption or decrease in the current flow therethrough, resulting in a measurable current variation as is depicted in the waveform 34 at the bottom of the figure. As the portions 30 of the biomolecule 14 that include probes 12 pass through the nanopore 20, the current is partially interrupted forming a relative trough 36 in the recorded current during passage of the bound portion 30. Similarly, as the unhybridized portions 32 of the biomolecule 14 pass, the current remains relatively high forming a peak 38 in the measured current. The electrodes 28 installed in the cis 24 and trans 26 chambers detect and reflect these variations in the monitored current. Further, the measurements of the current variations are measured and recorded as a function of time. As a result, the periodic interruptions or variations in current indicate where, as a function of relative or absolute position, the known probe 12 sequence has attached to the biomolecule 14.

Figure 7:
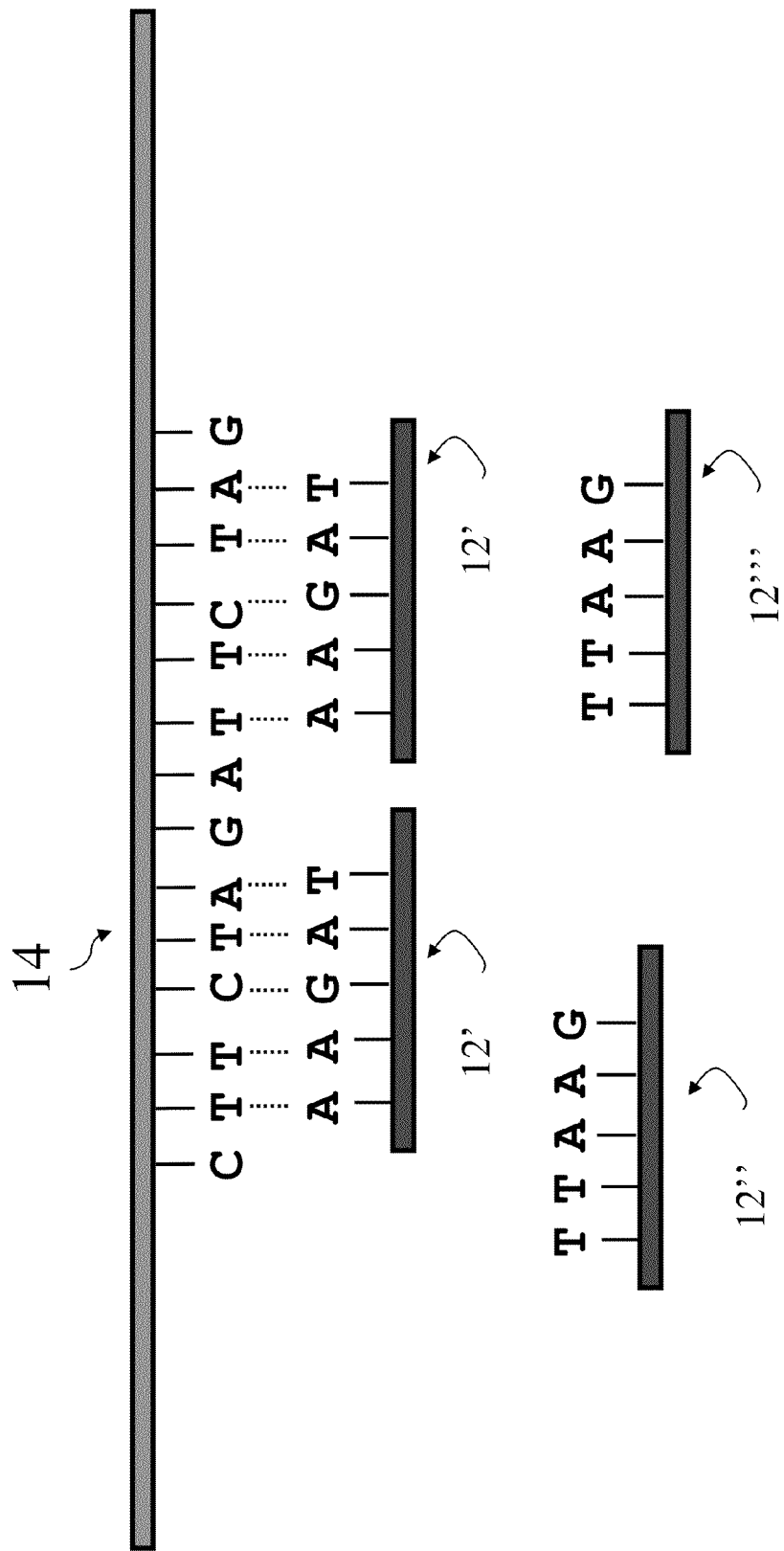
FIG. 7 depicts the results from a repetitive application of the disclosed method using different probes (SEQ ID NO: 3)

The measurements obtained and recorded, as well as the time scale, may be input into a computer algorithm that maps the binding locations of the known probe 12 sequences along the length of the biomolecule 14. Once the probe 12 locations are known, since the probe 12 length and composition is known, the sequence of the biomolecule 14 along the portions 30 to which the probes 12 were attached can be determined. This process can then be repeated using a different known probe 12. Further, the process can be repeated until every probe 12 within the library of n-mer probes has been hybridized with the biomolecule 14 strand of interest. It can be seen in FIG. 7 that by repeating the process with different known probes 12', 12" and 12''', the gaps in the portions of the biomolecule 14 are gradually filled in with each subsequent hybridization and sequencing step until eventually the entire sequence of the biomolecule 14 of interest is known.

Each subsequent hybridization and sequencing of the biomolecule 14 may be accomplished in a variety of ways. For example, a plurality of nanopore assemblies, each sequencing copies of the same biomolecule of interest using different known probes, may be utilized simultaneously in a parallel fashion. Similarly, the same biomolecule may be repetitively hybridized and sequenced by passing it through a series of interconnected chambers. Finally, any combination of the above two processes may also be employed.

Detection of variations in electrical potential between the cis and trans chambers as the hybridized biomolecule 14 of interest passes through the nanopore 20 may be accomplished in many different ways. For example, the variation in current flow as described above may be measured and recorded. Optionally, the change in capacitance as measured on the nanopore membrane itself may be detected and recorded as the biomolecule 14 passes through the nanopore. Finally, the quantum phenomenon known as electron tunneling may be measured, whereby electrons travel in a perpendicular fashion relative to the path of travel taken by the biomolecule. In essence, as the biomolecule 14 passes through the nanopore 20, the probe 12 locations bridge the nanopore 20, thereby allowing electrons to propagate across the nanopore in a measurable event. As the electrons propagate across the nanopore, the event is measured and recorded to determine the relative probe binding locations. The particular method by which the electrical variations are measured is not important, only that fluctuation in electrical properties is measured as they are impacted by the passing of the biomolecule through the nanopore.

The way in which the electrical potential varies, as a function of time, may depend on whether a single-stranded (unhybridized) or double-stranded (hybridized) region of the biomolecule is passing through the nanopore 20 and may be complicated. In the simplest scenario, the double-stranded region 30 may suppress the current in comparison to the single-stranded region 32, which may suppress the current in comparison to when no biomolecule 14 is translocating. However, for small nanopore 20 dimensions or low salt concentrations, the current may be augmented with the translocation of double-stranded portions 30. In this case, the points of increased current may be used as an indicator of where the probes 12 are positioned along the biomolecule 14.

The recorded changes in electrical potential across the nanopore 20 as a factor of time may then processed using a computer and compiled using the sequences of the known probes 12 to reconstruct the entire sequence of the biomolecule 14 strand of interest.

In one embodiment, the biomolecule to be sequenced may be double-stranded DNA. The sequencing method may include forming local ternary complexes along the length of the double-stranded target molecule using one or more probes and obtaining information about the location of the probe(s) using a detector. These methods may be implemented with nanopore (including micropore) detection systems. Double-stranded DNA, in contrast to single stranded DNA, does not have a tendency to fold into secondary structures, may be easier to manipulate prior to the introduction into a nanopore channel, has a consistent transmission speed through nanopore channels, and has a longer persistence length. In addition, higher affinity probe molecules with greater sequence selectivity may be used with double-stranded DNA, than with single-stranded DNA.

Illustrative embodiments described herein relate to detecting and analyzing probe maps to gather sequence information. More particularly, illustrative embodiments described herein relate to creating and detecting specific ternary complexes along double-stranded biopolymer target molecules to gather sequence information. For simplicity, the embodiments described below use DNA as a target, but other biopolymers such as RNA may also be sequenced. In an embodiment, probes that are selective for one or more sequences may be hybridized to a target sequence. The target sequence may be double-stranded DNA and the probes may be chosen for the ability to bind to one or more sites of double-stranded DNA. The binding of the probe may then be detected using a nanopore to generate a probe map in computer media. By detecting probe binding at multiple subsequences along the target, a spectrum map may be constructed. Information contained in the spectrum map may then be aligned an assembled into a finished sequence.

Like Sequence-by-Hybridization (SBH), positional hybridization sequencing relies on the biochemical hybridization of probes to an unknown target. However, once the biochemical hybridization is substantially complete, a detector that determines the position of hybridization may be utilized. In addition to determining the position of hybridization, the detector may be capable of counting the number of times a probe hybridizes to the target. The positional information allows a combinatorial sequence reconstruction algorithm to be used that differs from those used in SBH. In standard SBH, the spectrum of the target sequence from which probes are selected during each step of sequence reconstruction includes all the probes that hybridized and this remains constant during the course of the reconstruction. Thus, every probe in the spectrum can be used at any step during reconstruction. In the case of positional hybridization detection, the spectrum may be a dynamically weighted spectrum. The dynamically weighted spectrum may include all the probes that bound to the target (with different weights). However, in most embodiments, the dynamically weighted spectrum may only include a subset of the spectrum. A consequence of not including all the probes may be that during reconstruction of the sequence, the dynamically weighted spectrum has to change at least once in order to encompass all probes in the spectrum.

Other illustrative embodiments relate to methods and computer algorithms for aggregating, aligning and assembling multiple probe maps into a model nucleotide sequence. In a specific embodiment, a combinatorial sequence reconstruction algorithm may be used to generate spectrum maps for determining sequence information. Due to the complex nature of the calculations and quantity of data generated, the methods described herein may be carried out in a substantially automated manner by an appropriate computer algorithm running on a computer of adequate speed.

In an illustrative embodiment, detection of local ternary complexes may be accomplished by passing double-stranded biopolymer target molecule or fragment thereof through a nanopore and detecting an electrical signal indicative of the locations of the local ternary complexes along the double-stranded biopolymer target molecule. The use of nanopores to detect solution phase DNA hybridization reactions is described in U.S. Pat. No. 6,537,755 to Drmanac, and in U.S. Patent Application Publication No. 20060287833, to Yakhini; both citations are incorporated in their entireties by reference herein.

Figure 8:
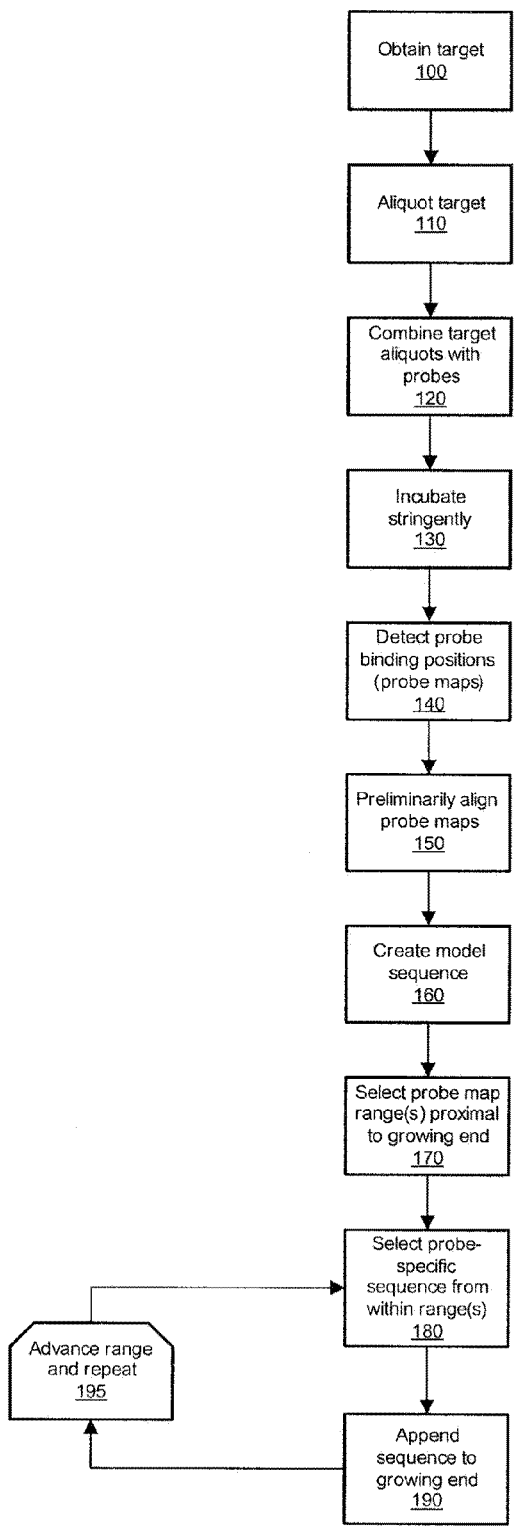
FIG. 8 is a flow chart for a method of sequencing DNA.

FIG. 8 shows a flow chart for a method of sequencing a target. For simplicity, this and other embodiments detailed herein use genomic DNA as the target to be sequenced, although other types of molecules, including cDNA, and RNA could be sequenced in this way. A target DNA sequence may be extracted from a source and purified (step 100). The starting material may be any of a variety of single or double-stranded nucleic acids, for example, genomic DNA, PCR products, cDNA, RNA-DNA hybrids and the like. The use of double-stranded DNA as a target has several advantages over the use of single stranded DNA. These include a reduction in the amount of secondary structure present in the target strand to be sequenced, a more consistent transmission speed of the DNA through the nanopore, the ability to manipulate single molecules of double-stranded target DNA prior to introduction into the nanopore, a longer persistence length of the DNA, and the use of probe molecules that are of higher affinity and sequence selectivity. While the method may be most powerful with long pieces of DNA to which a probe may bind in multiple subsequence positions, the method may also be applicable to shorter nucleic acids such as viral genomes, plasmids, cosmids, etc. The target DNA may be derived from any of multiple sources and may be the genome of an organism whose DNA sequence is unknown, or is known (resequencing). Alternatively, the DNA may be derived from several organisms. The target DNA may be of a known size or range of sizes; alternatively, the size of the target DNA may be unknown. The purification of step 100 may be the complete purification step or performed in conjunction with later steps. For example, a biochip that includes a nanopore may also accomplish further purification via electrophoretic or other methods. Optionally, the target may be amplified by PCR, rolling circle amplification, or other suitable method.

If chromosomal DNA or other large target DNA polymers are to be sequenced, it may be desirable to fragment the DNA. Target DNA may be fragmented by any of a number of commonly used methods including hydrodynamic shearing, sonication, ultrasonic fragmentation, enzymatic cleavage, nebulization, chemical cleavage, and heat induced fragmentation. Hydrodynamic shearing may be favorable if large nucleic acid fragments are desired. A commercially available device, HydroShear (Genomic Solutions, Ann Arbor, Mich., USA), is available that will shear DNA to a tight size distribution. To use this device, double-stranded DNA in solution is passed through a tube with an abrupt constriction. Fluid accelerates to maintain the volumetric flow rate through the smaller area of the constriction. During this acceleration, drag forces stretch the DNA until it snaps. The DNA fragments until the pieces are too short for the shearing forces to break the chemical bonds. The flow rate of the fluid and the size of the constriction determine the final DNA fragment sizes. In one configuration of the device, size ranges of sheared DNA of from 650 base pairs to 40,000 base pairs are achievable. In a second configuration of the device, size ranges of 1,000 base pairs to 9,000 base pairs are achievable.

The target DNA may then be aliquoted (step 110) and combined with probe molecules (step 120). For example, a first aliquot may be combined with a solution containing molecules of probe specific for a first target subsequence (e.g., a 5 to 20 base pair subsequence) and a second aliquot may be combined with a probe that is specific for a second target subsequence. In a simple scheme, the number of aliquots may be equal to the number of different probes to be used in the experiment. A single probe (i.e., a collection of probe molecules having the same or functionally equivalent sequence specificity) may then be added to each aliquot of the target DNA. Alternatively, the number of aliquots may be smaller or larger than the number of different probes; a mixture of probes may be added to each aliquot. The probes may be of either uniform or differing lengths. Various mixing procedures may be used to combine the target and probe, but if the procedure is performed at very low volumes (e.g., 0.1-10 nanoliter), diffusional mixing may suffice.

The aliquots may then be incubated under stringent conditions (step 130) to allow the probe molecules to sample multiple subsequences and to approach equilibrium in finding energetically favored subsequences to bind to (i.e., the subsequences for which the probe is specific). In other words, each aliquot containing target DNA and a probe or a mixture of probes may be incubated under conditions that result in greater hybridization of probes to matched recognition sequences than to sequences containing a mismatch. Taking into account the type of probe used, stringency may be adjusted through temperature, salt concentrations, addition of organic solvents, washing with solutions, electrophoretic washing, or other methods. Optionally, incubated aliquots may be combined prior to analysis, especially if tagged probes are used. A formation of specific local probe-target complexes, may result, which, as described below, may be modeled as a probe map (step 140). In specific embodiments, the probe map includes the relative positional information of the local ternary complexes along the double-stranded biopolymer, the absolute positional information of the local ternary complexes along the double-stranded biopolymer, and error of positional information of the local ternary complexes along the double-stranded biopolymer. In another embodiment, a second probe specific for one or more second recognition sites of the target molecule may be used to generate a second probe map. In yet another embodiment, two or more probes may be used for the detection of local ternary complexes, and for the generation of two or more probe maps.

The collection of hybridized or otherwise bound probes and positions may be used to form a model probe map of the target DNA. The probe map may be used to reconstruct the target DNA sequence. For example, multiple probe maps from probes having a variety of sequence specificities may be aligned and assembled to reconstruct a sequence. In an embodiment, n-mer probes may be used (e.g., polynucleotide probes), each probe having a specificity for one of $4^n$ possible DNA sequence combinations. A complete library of $4^n$ n-mer probes may be utilized to give complete target sequence coverage. In illustrative embodiments, n may be from 3 to 10.

Since the target was fragmented, the complete probe map may be constructed from data derived from the multiple fragments. The probe map may be assembled by matching the pattern between overlapping regions of multiple fragments to arrive at an aggregated hybridization pattern for a given probe having a given target specificity. The pattern matching routine may include determining the 3'→5' orientation of each hybridization pattern, especially if this has not been determined previously, e.g., by comparison to a known sequence in a resequencing operation.

The sequence specificity of a probe, combined with its estimated probe map with respect to the target, yields a partial sequence model of the target. In other words, if a probe-target complex is detected, it may be expected that the target sequence contains the subsequence for which a given probe is specific. For sufficiently short probes, this subsequence may be repeated multiple times in the target at positions corresponding to the positional information that should be available from detection of binding of that probe. The subsequences may be assigned relative positional information by making use of the distances of measured uncomplexed regions intervening between the probe binding sites. The positional information may contain some error however.

The model sequences derived from the probe map of multiple probes having multiple corresponding sequence specificities may be preliminarily aligned with respect to each other and/or with respect to other landmarks (step 150). For example, for resequencing operations, the sequences may be aligned based on a maximal overlap with a known sequence. Alternatively, the model sequences may be aligned based on maximal overlap with each other or with respect to bound proteins (e.g., zinc finger proteins) included in the mixture, or with respect to other sequence landmarks.

A starting model sequence may be created (step 160). For example, a starting sequence may be created using the known sequence specificity of one of the probes for which a probe map has been determined. The chosen probe may be located at or near the 3' or 5' terminus of the preliminarily aligned spectrum map. A growing-end may be chosen for the starting sequence, on the internal side.

In certain embodiments, a spectrum map may be generated from at least a first probe map and a second probe map. Determining the spectrum map may include using a combinatorial sequence reconstruction algorithm. Determining the spectrum map may also include determining a candidate sequence by ordering at least two probe sequences using positional information and error of positional information. If the first recognition site sequence and the second recognition site sequence overlap, determining the spectrum map may include aligning the recognition site sequences.

A weighted spectrum may be chosen as a subset of the spectrum map with respect to the growing end (step 170). The probes encompassed in this subset of the spectrum may be selected using positional information or some parameter related to positional information generated during the detection step. The various sequences corresponding to the probe-specificities for the probes for which binding events were detected within the weighted spectrum may then be compared with a sequence of the growing end (in the initial stages of the process, this may be the entire starting sequence). If possible, a sequence may be chosen that has maximal identity for the growing end yet extends at least one nucleotide beyond the growing end (step 180). At least one base of the non-overlapping sequence may then be appended to the growing end (step 190). The weighted spectrum may then be changed. This process of selecting nucleotides, appending nucleotides, and changing the weighted spectrum may be repeated until sufficient sequence is determined or the data set is exhausted (step 195). If more than one nucleotide choice is available for appending, this may be resolved by evaluating each possible choice in terms of maximal overlap for the next few sequence extensions.

Contrastingly, in standard SBH, the weighted spectrum of the target sequence from which probes are selected during each step of sequence reconstruction may be exactly equal to the spectrum of the target. Every probe in the spectrum may be used at any step during reconstruction. In the case of positional hybridization detection, the weighted spectrum of the target sequence encompassing probes selected during each step of reconstruction may be smaller than the length of the target strand. The weighted spectrum may be as large as the spectrum of the target minus one probe. However, in some embodiments, the weighted spectrum may be significantly smaller than the target spectrum. Thus, during reconstruction of the sequence, the weighted spectrum has to change at least once in order to encompass all probes in the spectrum.

If there were no error in the probe maps with regard to the position of hybridization of the probe, the weighted spectrum may consist of only one probe. Some error may be expected, however. At the other extreme, if there were no certainty regarding the position of probe locations in a probe map, then the next nucleotide to be appended may logically be selected from any probe binding to the target. This corresponds to standard SBH. Balancing these two extremes, the weighted spectrum may be optimized based on estimated error in the positional information contained in each probe map or in the spectrum map. For example, a standard deviation, variance or other quantitative measurement of the error in one or more probe locations may be calculated based on the detector output. The weighted spectrum may then be set to be a multiple of this estimated error. Accordingly, the number of probes encompassed by the weighted spectrum and the size of the error may be inversely proportional, or otherwise inversely correlated. Simply stated, a larger weighted spectrum may be used when a larger positional error is present. The weighted spectrum may be expressed in terms of probes that fall within a fixed number of nucleotides distance from the growing end. Alternatively, the range may vary based on the error in the positional information for each probe, or even based on the estimated error at each probe binding site.

Other alternative calculation methods may be employed including adaptive or genetic algorithms that adjust based on the quality of the sequence output. The output of multiple such methods may also be compared and the best one selected. The range or ranges may be calculated once, multiple times during the procedure, or after each nucleotide is appended.

A number of types of molecules are known to bind in a sequence-specific fashion to double-stranded DNA and may be used as probes individually or in combination. The molecules may be composed of one or more moieties such as polyamides, a nucleic acid, and/or a peptide nucleic acid. In a specific embodiment, the molecule may be a gapped polyamide molecule such as those described in the following Dervan references, each of which is incorporated in its entirety by reference herein: Dervan, P. B. Molecular Recognition of DNA by Small Molecules. *Bioorg. Med. Chem.* 2001, 9, 2215-2235; and Dervan, P. B.; Edelson, B. S. Recognition of the DNA minor groove by pyrrole-imidazole polyamides. *Curr. Op. Struc. Biol.* 2003, 13, 284-299.

Alternatively, the probe molecules may be composed of native or modified DNA oligonucleotides that are capable of binding in a triple stranded fashion with double-stranded DNA. Alternatively, the probe molecules may be nucleic acid molecules that are combined with the target in the presence of a recombinational enzyme or a recombinational protein. The probe molecule may be a peptide nucleic acid capable of binding to double-stranded DNA. Other modified oligonucleotides, proteins, peptides, or other polymers may also be capable of binding to double-stranded DNA in a sequence specific fashion and thus may be used.

In an embodiment, the probes may be polyamides that bind in a 2:1 complex with dsDNA in the minor groove of the DNA. Alternatively or in addition, the polyamide may bind to the DNA in a 1:1 complex or in a 2:1 or higher-order complex. In the case of a 2:1 complex, the two polyamides may be separate molecules or may be covalently joined at the ends or in the middle of the molecules to form hairpin polyamides, cyclic polyamides, H-pin motifs, or U-pin motifs. Charged groups may be placed at either end or in the middle of the polyamides in order to change their affinity for target or for other probe molecules. Linkers may be attached between heterocycles in the polyamide to modulate the curvature of the molecule. Curvature modulation may be used to increase the binding affinity of a polyamide to a longer DNA sequence by matching the curvature of the polyamide to the curvature of the DNA molecule. Other linkages and appendages may also be used.

Polyamide probes may consist of imidazole, pyrrole, hydroxy-pyrrole, benzimidazole, and hydroxybenzimidazole heterocycles. The heterocycles may be substituted with alkyl or functional groups in order to modulate their binding to DNA. Other heterocycles may also be used. Pairing rules of polyamides for minor groove recognition of DNA have been described by Dervan (see Dervan, P. B.; Edelson, B. S. Recognition of the DNA minor groove by pyrrole-imidazole polyamides. Curr. Op. Struc. Biol. 2003, 13, 284-299).

Generally, each aliquot of target DNA may be subsequently analyzed to detect binding of the probe to the target DNA. In a specific embodiment, a probe map may be generated for each probe to give absolute or relative positional information of probe binding sites located on a longer stretch of dsDNA. The probe binding sites may be separated by non-binding, uncomplexed regions of the target that have relatively low affinity for the probe. Accordingly, the probe map may include absolute or relative information related to the location and length (e.g., in base pairs) of the uncomplexed regions.

A single molecule detector may be used to detect probe binding and thus arrive at a probe map. Unlike detectors typically used for SBH, the single molecule detector may determine the number of times that a given probe binds to a target molecule and the absolute or relative binding sites for that probe. For example, a nanopore based detector, a field effect transistor, Coulomb-charging based detector, or scanning-tunneling or force microscope may be used. Multiple such detectors may be used in parallel or in series. Data from multiple detectors may then be aggregated for analysis, including correlation analysis. Each mixture may be independently analyzed. In an embodiment of the technique, a nanopore may be used to detect the position of local ternary complexes on the target DNA.

In certain embodiments, a nanopore-based detector detects temporal changes in current as probe-complexed and uncomplexed stretches of double-stranded DNA pass through the pore. As seen for single-stranded DNA, the change in current may be positive or negative depending on the concentration of ions in the buffer on either side of the nanopore. The current may increase or decrease while a probe is passing through the pore due to blockade current, tunneling current or other mechanism.

A current signal, reflecting a change in impedance or current measured by the nanopore detector, may be monitored to gain information about the presence and spacings of hybridized probes. As an analyte moves through a volume monitored by the nanopore detector, the current signal changes. The signal may be elevated or depressed for a period of time that reflects the length of the analyte, e.g., a probe-target complex, or the length of the intervening regions without probes. A typical analyte may impede the flow of ions in the electrolyte and be non-conductive. Therefore, the current typically decreases as the analyte flows through the sensing volume. In some embodiments, e.g., a low salt electrolyte and a charge-carrying analyte, the current signal may increase as the analyte flows through the sensing volume. The current signal further changes when the portion of the analyte containing the hybridized probe moves through the volume between the sensing electrodes.

A time interval between current signal changes may be recorded. The duration of the change in the current signal may indicate a presence of a hybridized probe. This duration may be used to determine a distance between two probes on the biopolymer. To determine the distance, one may calibrate the system with known standards and calculate an average speed for the analyte in the channel. Time would then be directly related to distance. In embodiments with multiple hybridized probes, multiple peaks may form, with each peak corresponding to a hybridized probe, with the time between peaks being indicative of the relative spacing of the hybridized probes.

Similarly, the duration of a change in the current signal may be used to determine a length of the analyte.

In a certain embodiment, the biopolymer target molecule may be single-stranded DNA (ssDNA). Double-stranded DNA may be generated from the single-stranded template by enzymatically synthesizing the second strand and thereby afford may of the aforementioned benefits of using dsDNA: a reduction in the amount of secondary structure present in the target, a more consistent transmission speed of the DNA through the nanopore, the ability to manipulate single molecules of target DNA prior to introduction into the nanopore, and a longer persistence length of the DNA. In an alternative embodiment, ssDNA may be stabilized using a plurality of single-stranded DNA binding agents to stabilize the single stranded DNA. The binding agent molecules may be nonspecific, or may be chosen to have specificity for various DNA target subsequences. For example, a mixture of tens, hundreds, or thousands of short (e.g., designed to bind to 6-mers) DNA, or DNA analogs designed to target particular target subsequences may be stringently incubated with a target ssDNA sample. One or more detection probes may then be added and the mixture incubated under stringent conditions. The mixture may be chosen so as to not preclude a detection probe from binding to its complementary subsequence. Different stabilizing agent mixtures may be used with additional aliquots containing target combined with additional detection probes having different subsequence specificity. In related embodiments, the mixtures of stabilizing agents may be chosen to be non-overlapping in their sequence specificity. Using locked nucleic acid or peptide nucleic acid probes may allow the use of more stable probes, capable of binding in higher stringency conditions (e.g., high temperature or low-salt). As a result, the mixture may require fewer agents; e.g., a mixture may be sufficient that binds to only a third or less of the ssDNA sequence.

Figure 9:
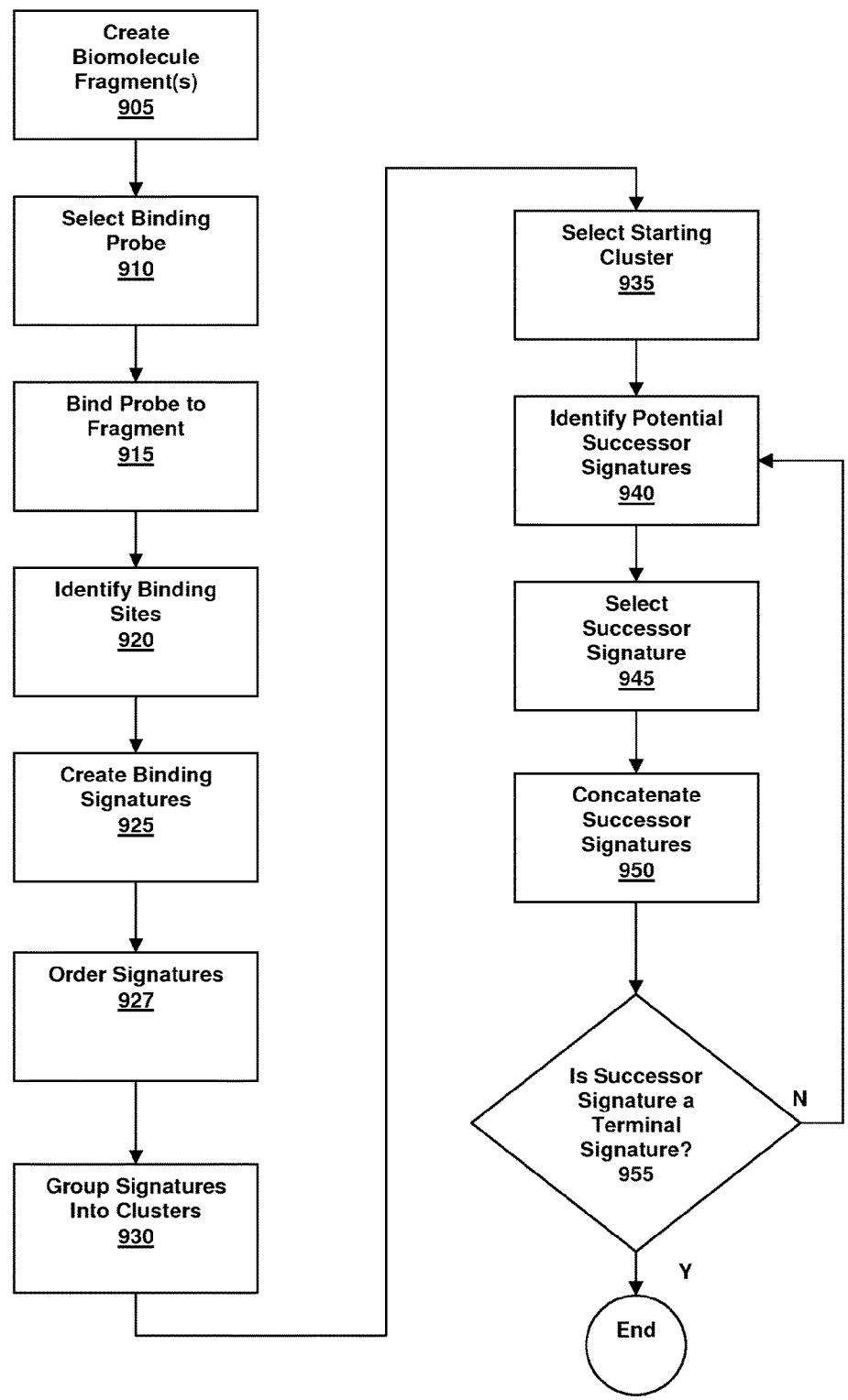
FIG. 9 is a flow chart for a method of sequencing a biomolecule in accordance with an embodiment of the present invention.

Referring to FIG. 9, the above techniques may be used to sequence a biomolecule. The biomolecule may, for example, be a chromosome, single or double-stranded DNA molecule, RNA molecule, or other complex biomolecule comprising a large number of nucleotides or other identifiable components that occur in a random (or seemingly random) sequence. The sequence may represent an entire biomolecule or, in some cases, portions of a biomolecule.

In one embodiment, fragments are drawn from biomolecules at random locations with the goal of aligning and merging maps of these fragments into maps of the entire biomolecule. The fragments may be of any length. For example, fragments may range from 50,000 characters to 100,000 characters, from 100,000 characters to 250,000 characters, or over 250,000 characters. In one particular embodiment, a fragment length of 100,000 characters is used.

Uniform binding probes are introduced to a particular fragment such that the probes bind to the fragment according to binding pair rules. The binding probes may also be of any length, but are typically shorter than the length of the fragment. In certain embodiments, the probes are significantly shorter such that there may be tens or hundreds of possible binding sites on one fragment. In one particular implementation, the probes are six characters long. In other embodiments, the probe length may range between seven and fifteen characters. Probes need not be of uniform length and may be any sequence of characters that will bind to the fragments. In certain embodiments, the probes may be proteins or enzymes that, based on their character sequence, selectively bind to the fragment or have enzymatic activity that depends on a particular sequence in the biopolymer, such as certain restriction enzymes. The restriction enzymatic activity may be inhibited by removing magnesium from the solution containing the fragment and the probes, for example. The detection of a restriction enzyme binding to DNA in the absence of magnesium may then assist with the mapping of the biomolecule.

The positions within the fragment at which the probes bound to the fragment are identified as binding sites, and the distances between the binding sites are measured using the methods described above. The measured distances may include an error, which may be the same or different for different probes. For each fragment and probe, a collection of binding signatures is created, each of which identifies the fragment, the probe, and the distances (also referred to as "intervals") between adjacent binding sites in a contiguous portion of the fragment. In some cases, the intervals are measured in "base pairs" that occur between binding sites. The binding signature may be of any length and include any number of biding sites. In certain implementations, using nine binding sites and eight intervals has provided statistically accurate results. The length of the fragment(s) and probes may also be modified such that the resulting vector of intervals for any particular fragment-probe paring is sufficiently distinct from other binding signatures.

The binding signatures are ordered in a table based on one or more features of the signatures, such as the total length of the signature. Alternatively, the ordering may be by the length of the first interval in the signature. Once ordered, the binding signatures are grouped into one or more clusters based, in some cases, on the match between the distances between the binding sites within each fragment. For example, a particular signature may be {12835; 3524; 6420; 4082; 128; 644; 8922; 1121}. Other signatures having similar distance measurements and ratios such as {12840; 3500; 6415; 4078; 132; 650; 8920; 1120} may be identified as "close" and therefore placed in a common cluster. In another embodiment, the variance between intervals within each signature is determined, and may be used to cluster the signatures either independently or in conjunction with the intervals.

In one particular implementation, a pair of signatures a and b are considered to match if, for all intervals i, $|a.d_i - b.d_i| < s \ast \sqrt{k} \ast \sqrt{MIN(a.d_i, b.d_i)}$, where k is a constant s is a number of standard deviations optimized to capture most matches. The following pseudocode may be used to build signature clusters:

```
i:=0
while I <= n−1
    for (j := i+1 to n−1) and ( |sig[i].1 − sig[j].1| <
        s*√k*√MIN(sig[i].1, sig[j].1) )
        if (sig[i] matches sig[j])
            add sig[j] to cluster sig[i]
            if (j = i+1)
                i := j
```

In some cases, all signatures have lengths within a range of $s \ast \sqrt{k}$, in which case $O(n^2)$ comparisons are made. At the opposite extreme, signatures may have widely dispersed lengths, in which case the number of comparisons can be limited to one per signature, by virtue of always advancing loop variable i with j and terminating the j loop immediately after the first non-matching signatures.

Figure 10:
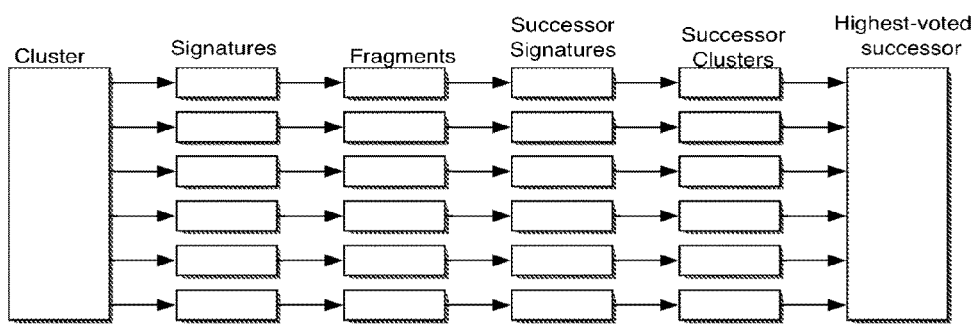
FIG. 10 illustrates a process for selecting successor signatures from clusters of signatures according to one embodiment of the invention.

Referring to FIG. 10, a complete mapping of the biomolecule may be built by combining a sequence of signatures based on known predecessor-successor relationships for each signature in its origin fragment. Initially, a starting cluster is selected, either based on predetermined selection criteria or at random. The process of moving along the biomolecule may proceed either forward (e.g., to the "right" as one reads the characters in a DNA molecule, for example) or backward.

In one example, a signature cluster is selected at random. Each signature in a cluster has a set of distances that are very close to a cluster consensus. Each signature in the cluster points to a single fragment from which that signature was derived and has a single successor signature in that fragment. Further, each successor signature is associated with a single signature cluster. By tallying the highest-voted (i.e., the most frequently identified) signature cluster from all the potential successors a new cluster is selected.

As an example, one signature may be (12832; 3530; 6426; 4074; 126; 647; 8929; 1118), as generated from a particular fragment whose vector of distances are: (2206; 4073; 3680; 439; 1450; 12832; 3530; 6426; 4074; 126; 647; 8929; 1118; 6846; 1236; 6363; 1664; 54). The sub-vector (12832; 3530; 6426; 4074; 126; 647; 8929; 1118) is considered the origin of the signature at hand, and by moving one binding site forward, the successor signature is (3530; 6426; 4074; 126; 647; 8929; 1118; 6846). Therefore, the cluster that includes this signature gets one vote from the current signature. Looping through all signatures in the current signature cluster produces a collection of votes for subsequent signature clusters. The signature cluster receiving the most votes becomes the current signature cluster for the next iteration.

Chaining forwards and backwards from the initial cluster creates a complete map of the biomolecule assuming the successor signature voting identifies the correct successor. Since the difference, on any given fragment, between a signature and its successor is only one probe landing, the probability of a correct signature is just under 90%. So an incorrect majority vote takes place at probability $\text{sum}\_i=0.[c/2](0.1^i)*(0.9^{(c-i)})*(c \text{ choose } i)$. Under current parameter estimates, this is $\sim 10^{-12}$ for $c=50$.

The functionality described above may be implemented in hardware or software, or a combination of both on a general-purpose computer. In addition, such a program may set aside portions of a computer's random access memory to provide control logic that affects one or more of the image capture, user input (using, for example, a mouse, keyboard or pointing device) and presentation on a display.

The program may be written in any one of a number of high-level languages, such as FORTRAN, PASCAL, C, C++, C#, Java, Tcl, or BASIC or development environments such as Flash, Ruby on Rails, etc. Further, the program can be written in a script, macro, or functionality embedded in commercially available software, such as EXCEL or VISUAL BASIC. Additionally, the software can be implemented in an assembly language directed to a microprocessor resident on a computer. For example, the software can be implemented in Intel 80x86 assembly language if it is configured to run on an IBM PC or PC clone. The software may be embedded on an article of manufacture including, but not limited to, "computer-readable program means" such as a floppy disk, a hard disk, an optical disk, a magnetic tape, a PROM, an EEPROM, or CD-ROM.

Those skilled in the art will readily appreciate that all parameters listed herein are meant to be exemplary and actual parameters depend upon the specific application for which the methods and materials of the present invention are used. It is, therefore, to be understood that the foregoing embodiments are presented by way of example only and that, within the scope of the appended claims and equivalents thereto, the invention may be practiced otherwise than as specifically described.

What is claimed is:

1. A method for determining a sequence of a biomolecule, the method comprising the steps of:
   a) creating a biomolecule fragment from the biomolecule;
   b) binding a plurality of uniform probes having the same sequence and length to the biomolecule fragment;
   c) identifying a plurality of binding sites along the biomolecule fragment at which the probes bind to the biomolecule;
   d) creating a collection of binding signatures for the biomolecule fragment, each binding signature representing a series of distances between binding sites within the fragment;
   e) grouping the binding signatures into a plurality of signature clusters based at least in part on distances between the binding sites in each binding signature;

f) for each binding signature in a first cluster, selecting a potential successor binding signature from signature clusters other than the first signature cluster;
g) identifying one of the potential successor binding signatures as a successor binding signature;
h) repeating steps f) and g) until the successor signature represents a terminal signature, resulting in a sequence of signatures representing at least a portion of the biomolecule.

2. The method of claim 1 further comprising measuring the distances between the binding sites within the fragment.

3. The method of claim 1 further comprising assigning an error to each measured distance between binding sites.

4. The method of claim 2 wherein the distances are measured based on a number of base pairs between the binding sites.

5. The method of claim 2 wherein measuring the distances between the binding sites further comprises measuring electrical signals emitted by the fragment as the fragment passes through a nanopore.

6. The method of claim 1 further comprising ordering the signatures based on one or more characteristics of the signatures.

7. The method of claim 6 wherein the characteristics of the signatures comprise a total length of the signature.

8. The method of claim 1 wherein the biomolecule comprises a single-stranded DNA molecule.

9. The method of claim 1 wherein the biomolecule comprises a double-stranded DNA molecule.

10. The method of claim 1 wherein the signature clusters are determined based on a degree of match between the binding sites attributed to the binding signatures.

11. The method of claim 1, wherein the probes are selected from the group consisting of 6-mer probes, 7-mer probes, 8-mer probes and 9-mer probes.

12. A system for determining a sequence of a biomolecule, the system comprising:
 a) an identifying module that identifies a plurality of binding sites along a fragment of the biomolecule at which a plurality of uniform probes having the same sequence and length are bound;
 b) a signature-creating module that creates a collection of binding signatures for the fragment, each binding signature representing a series of distances between binding sites within the fragment;
 c) a grouping module that groups the binding signatures into a plurality of signature clusters based at least in part on distances between the binding sites in each binding signature;
 d) a selecting module that selects, for each binding signature in a first cluster, a potential successor binding signature from signature clusters other than the first signature cluster; and
 e) a sequencing module that (i) identifies one of the potential successor binding signatures as a successor binding signature, and (ii) determines the sequence of at least a portion of the biomolecule based at least in part on a series of identified successor binding signatures.

13. An article of manufacture having computer-readable program portions embodied thereon for sequencing a biomolecule, the article comprising computer-readable instructions for:
 a) creating a biomolecule fragment from the biomolecule;
 b) binding a plurality of uniform probes having the same sequence and length to the biomolecule fragment;
 c) identifying a plurality of binding sites along the biomolecule fragment at which the probes bind to the biomolecule;
 d) creating a collection of binding signatures for the biomolecule fragment, each binding signature representing a series of distances between binding sites within the fragment;
 e) grouping the binding signatures into a plurality of signature clusters based at least in part on distances between the binding sites in each binding signature;
 f) for each binding signature in a first cluster, selecting a potential successor binding signature from signature clusters other than the first signature cluster;
 g) identifying one of the potential successor binding signatures as a successor binding signature;
 h) repeating steps f) and g) until the successor signature represents a terminal signature, resulting in a sequence of signatures representing at least a portion of the biomolecule.

14. An apparatus for sequencing a biomolecule, the apparatus comprising:
 a memory for storing code that defines a set of instructions; and
 a processor for executing the set of instructions to:
 (i) identify a plurality of binding sites along a fragment of the biomolecule at which a plurality of uniform probes having the same sequence and length are bound;
 (ii) create a collection of binding signatures for the fragment, each binding signature representing a series of distances between binding sites within the fragment;
 (iii) group the binding signatures into a plurality of signature clusters based at least in part on distances between the binding sites in each binding signature;
 (iv) select, for each binding signature in a first cluster, a potential successor binding signature from signature clusters other than the first signature cluster;
 (v) identify one of the potential successor binding signatures as a successor binding signature; and
 (vi) determine the sequence of at least a portion of the biomolecule based at least in part on a series of identified successor binding signatures.

* * * * *

UNITED STATES PATENT AND TRADEMARK OFFICE
CERTIFICATE OF CORRECTION

| | | |
|---|---|---|
| PATENT NO. | : 8,455,260 B2 | Page 1 of 1 |
| APPLICATION NO. | : 12/732259 | |
| DATED | : June 4, 2013 | |
| INVENTOR(S) | : Peter H. Goldstein et al. | |

It is certified that error appears in the above-identified patent and that said Letters Patent is hereby corrected as shown below:

On the Title page in item (73) Assignee, delete "Massachusetts Institute of Technology, Cambridge, MA (US)" and replace with:

--NABSYS, INC., Providence, Rhode Island (US)--

Signed and Sealed this
Thirteenth Day of August, 2013

Teresa Stanek Rea
*Acting Director of the United States Patent and Trademark Office*